United States Patent [19]

Shibahashi et al.

[11] Patent Number: 5,352,649
[45] Date of Patent: Oct. 4, 1994

[54] THERMOCHROMIC LAMINATE MEMBER, AND COMPOSITION AND SHEET FOR PRODUCING THE SAME

[75] Inventors: Yutaka Shibahashi, Nagoya; Michiyuki Yasuda, Gifu, both of Japan

[73] Assignee: The Pilot Ink Co., Ltd., Nagoya, Japan

[21] Appl. No.: 907,577

[22] Filed: Jul. 2, 1992

[30] Foreign Application Priority Data

| Jul. 4, 1991 | [JP] | Japan | 3-190988 |
| Nov. 22, 1991 | [JP] | Japan | 3-104113[U] |
| Nov. 22, 1991 | [JP] | Japan | 3-104114[U] |
| Nov. 22, 1991 | [JP] | Japan | 3-333974 |

[51] Int. Cl.$^5$ ............................................. B41M 5/40
[52] U.S. Cl. ........................ 503/207; 428/324; 428/403; 428/913; 503/200; 503/201; 503/226
[58] Field of Search ................ 427/152; 428/195, 207, 428/913, 324, 403, 914; 503/200, 201, 207, 226, 215

[56] References Cited

U.S. PATENT DOCUMENTS 4,028,118  6/1977  Nakasuji et al. .................. 102/21
4,920,991  5/1990  Shibahashi et al. ................ 132/73

FOREIGN PATENT DOCUMENTS 0382241  8/1990  European Pat. Off. ............ 428/913
2186516  1/1974  France ................................. 428/913

*Primary Examiner*—B. Hamilton Hess
*Attorney, Agent, or Firm*—Fitzpatrick, Cella, Harper & Scinto

[57] ABSTRACT

A thermochromic laminate member capable of reversible change from a metallic luster color to a colorless state, comprises a first layer for regulating the wavelength of reflected light, composed of a metal luster pigment, which consists of natural mica surfacially covered with titanium oxide and has a grain size of 5 to 100 μm, and a film forming material; and a second layer composed of a thermochromic material, which consists of an electron donating compound, an electron accepting compound, and an organic medium enabling a reversible color-forming reaction between said compounds and has a luminocity value of 6 or lower in the colored state and a luminocity value of 8 or higher in the colorless state, and a film forming material.

20 Claims, 2 Drawing Sheets

THERMOCHROMIC LAMINATE MEMBER, AND COMPOSITION AND SHEET FOR PRODUCING THE SAME

BACKGROUND OF THE INVENTION

1. Field of the Invention

The present invention relates to a metallically lustrous thermochromic laminate member of various metallic colors such as gold or silver, and a coating composition and a sheet adapted to be used in the preparation of said laminate member.

2. Related Background Art

Thermochromic materials showing reversible color change between a colored state and a colorless state or between a first colored state and a second colored state are already disclosed, for example, in the U.S. Pat. Nos. 4,028,118, 4,720,301 and 4,732,810, and thermochromic members employing such materials have been commercialized in the fields of temperature-indicators, toys, articles for magic etc.

However, there have not been known thermochromic materials that show, by a temperature change, a reversible color change between a metallic luster color such as gold or silver and a colorless state or another colored state, nor thermochromic members that clearly exhibit such color change.

An attempt to diversify the color change is disclosed in the Japanese Utility Model Publication No. 3-14400. The thermochromic member disclosed therein is formed by covering thermosensitive liquid crystal with a pearl luster layer, thereby realizing a color change with pearl luster.

However, since liquid crystal is basically colorless and only reflects a certain wavelength by selective scattering of the visible light, it requires a dark opaque layer in the back and therefore shows color changes of black-red-yellow-green-blue-purple-black. Consequently clear color changes cannot be realized when a pearl luster layer is provided thereon. For example, if a pearl luster gold-color pigment is employed, the colors appear in the order of gold, gold-toned red, gold-toned yellow, gold-toned green, gold-toned blue, gold-toned purple and gold, and there cannot be obtained a clear change to a color without gold tone. Also in case a pearl luster silver-color pigment is employed, the color changes in the order of silver, silvery red, silvery yellow, silvery blue, silvery purple and silver, without clear change to a color free from metallic luster. Also with other metallic luster pigments, the behavior is similar and there cannot be obtained clear change from a metallic luster color to a color without such metallic luster. It is furthermore not possible to achieve a change from the pearl luster color to a colorless state, nor to conceal or display the background color.

Since gold, silver and other metallic luster colors appear gorgeous, a color change from such metallic luster color to another color is most impressive to the spectators and has therefore been longed for in the thermochromic material.

SUMMARY OF THE INVENTION

The inventors have reached the present invention through an investigation to achieve effective color variation by the thermochromic material and to attain clear thermal change to various colors from gold, silver and metallic luster colors. Different from liquid crystal, the thermochromic material of the present invention shows a clear color change in itself, so that it does not requires a dark opaque background, and is still capable of showing a change between a colored state and a colorless state.

It is therefore possible to demonstrate a change from a metallic luster color to a colorless state by laminating a pigment layer of gold, silver or another metallic luster color on a colored-colorless varying layer employing the above-mentioned thermochromic material. It is also possible to demonstrate a change from a metallic luster color to white by forming the colored-colorless thermochromic layer on a white substrate and laminating a metallic luster pigment layer thereon. It is furthermore possible to demonstrate, to the observer, a clear change from a metallic luster color to another color by mixing a non-thermochromic coloring material. It is furthermore possible to conceal the underlying colored layer with the metallic luster color. These color changes or concealing action cannot be attained in the aforementioned system based on liquid crystal. Also the use of a thermochromic material with a large hysteresis, so-called color-memorizing heat-sensitive material, allows to retain the varied state after the removal of heat or coldness required for thermal color change and to demonstate such varied state in normal temperature range. Because of such clear thermal change of various metallic luster colors, the present invention is applicable to various fields of decoration, interior, toys, stationary and information.

The aspects of the present invention are as follows:

1. A thermochromic laminate member capable of reversible change from a metallic luster color to a colorless state, comprising:

A) a first layer for regulating the wavelength of reflected light, composed of a metal luster pigment, which consists of natural mica surfacially covered with titanium oxide and has a particle size of 5 to 100 μm, and a film forming material; and B) a second layer composed of a thermochromic material, which consists of an electron donating compound, an electron accepting compound, and an organic medium enabling a reversible color-forming reaction between said compounds and has a luminocity value of 6 or lower in the colored state and a luminocity value of 8 or higher in the colorless state, and a film forming material.

2. A thermochromic laminate member capable of reversible change from a metallic luster color to a colorless state, according to the aspect 1, comprising:

A) a first layer for regulating the wavelength of reflected light, selected from (a) a metallic luster coating obtained by a coating composed compound of a metal luster pigment, which consists of natural mica surfacially covered with titanium oxide and has a particle size of 5 to 100 μm, a film forming material and a vehicle; and (b) a metallic luster sheet molded from a metallic luster pigment, which consists of natural mica surfacially covered with titanium oxide and has a particle size of 5 to 100 μm, and synthetic resin; and B) a second layer selected from (a) a coated layer obtained from a coating composition composed of a thermochromic material, which consists of an electron donating compound, an electron accepting material and an organic medium enabling a reversible color-forming reaction between said compounds and has a luminocity value of 6 or lower in the colored state and a luminocity value of 8 or higher in the colorless state, a film forming material and a vehicle, and (b) a thermochromic sheet molded from a thermochromic material, which consists of an electron donating compound, an electron accepting compound and an organic medium enabling a reversible color-forming reaction between said compounds and has a luminocity value of 6 or lower in the colored state and a luminocity value of 8 or higher in the colorless state, and synthetic resin.

3. A thermochromic laminate member capable of reversible change from a metallic luster color to a dye or pigment color, according to the aspect 1 or 2, wherein the second thermochromic layer contains a non-thermochromic colored dye or pigment, and the mixture has a luminocity V1 of 6 or lower in the color-developed state and a luminocity V2 of 4 or higher in the color-diminished state, said luminocities satisfying a relation V2−V1>1.

4. A thermochromic laminate member capable of reversible change from a metallic luster color to a dye or pigment color, according to any of the aspects 1 to 3, further comprising a non-thermochromic colored layer, which is positioned next to the thermochromic layer of said laminate member, is composed of a non-thermochromic colored dye or pigment and a film forming material, has a luminocity V3 of color density of 4 or higher, and satisfies a relation V3−V4>1, wherein V4 is the luminocity of the thermochromic material in the color-developed state.

5. A thermochromic laminate member according to any of the aspects 1 to 4 and capable of reversible change from a metallic luster color to a colorless state or pale yellow or a dye or pigment color, wherein the thermochromic material consists of microcapsules enclosing an electron donating compound, an electron accepting compound and an organic medium capable of causing a reversible color-forming reaction of said compounds.

6. A thermochromic granular material formed into powder state by cutting the thermochromic laminate member according to any of the aspects 1 to 5 and capable of reversible change from a metallic luster color to a colorless state or a dye or pigment color.

7. A thermochromic fiber formed by cutting the thermochromic laminate member according to any of the aspects 1 to 5 and capable of reversible change from a metallic color to a colorless state or a dye or pigment color.

8. A two-liquid coating composition for forming a thermochromic laminate member capable of reversible change from a metallic luster color to a colorless state, consisting of:
A) a coating composition compound of a metallic luster pigment consisting of natural mica surfacially covered wiht titanium oxide, a film forming material, and a vehicle; and
B) a coating composition composed of a thermochromic material, which consists of an electron donating compound, an electron accepting material, and an organic medium capable of causing a reversible color-forming reaction between said compounds and has a luminocity value of 6 or lower in the color-developed state and a luminocity value of 8 or higher in the colorless state, a film forming material and a vehicle.

9. A two-liquid coating composition according to the aspect 8 and capable of reversible change from a metallic luster color to a dye or pigment color, wherein the coating composition composed of the thermochromic material, the film forming material and the vehicle contains a non-thermochromic colored dye or pigment, and the mixed system has a luminocity V1 of 6 or lower in the color-developed state, and a luminocity V2 of 4 or higher in the color-diminished state, said luminocities satisfying a relation V2−V1>1.

10. A three-liquid coating composition for forming a thermochromic laminate member capable of color change to a non-thermochromic dye or pigment color, comprising:
A) a coating composition composed of a metallic luster pigment consisting of natural mica surfacially covered with titanium oxide and having a particle size of 5 to 100 μm, a film forming agent and a vehicle;
B) a thermochromic composition selected from (a) a coating composition composed of a thermochromic material, which consists of an electron donating compound, an electron accepting compound and an organic medium capable of causing a reversible color-forming reaction of said compound sand has a luminocity of 6 or lower in the color-developed state and a luminocity of 8 or higher in the colorless state, a film forming material and a vehicle, and (b) a coating composition composed of a thermochromic material, which consists of an electron donating compound, an electron accepting compound and an organic medium capable of causing a reversible color-forming reaction of said compounds, and has a luminocity of 6 or lower in the color-developed state and a luminocity of 8 or higher in the colorless state, and a non-thermochromic colored dye or pigment, with the mixed system having a luminocity V1 of 6 or lower in the color-developed state and a luminocity V2 of 4 or higher in the color-diminished state, said luminocities satisfying a relation V2−V1>1; and
C) a coating composition composed of a non-thermochromic dye or pigment, a film forming material and a vehicle, having a luminocity V3 of 4 or higher and satisfying a relation V3−V4>1, wherein V4 is the luminocity of the thermochromic material in the color-developed state.

11. A coating composition according to any of the aspect 8 to 10, for forming a thermochromic laminate member capable of reversible change from a metallic luster color to a colorless or pale yellow state or a dye or pigment color, wherein the thermochromic material consists of microcapsules enclosing an electron donating compound, an electron accepting compound and an organic medium capable of causing a reversible color-forming reaction of said compounds.

12. A sheet for forming a thermochromic laminate member capable of reversible change from a metallic luster color to a colorless state, comprising a combination of:
A) a metallic luster sheet molded from a metallic luster pigment consisting of natural mica surfacially covered with titanium oxide and having a particle size of 5 to 100 μm, and a synthetic resin; and
B) a thermochromic sheet molded from a thermochromic material, which consists of an electron donating compound, an electron accepting compound, and an organic medium capable of causing a reversible color-forming reaction of said compounds and has a luminocity of 6 or lower in the color-developed state and a luminocity of 8 or higher in the colorless state, and a synthetic resin.

13. A sheet for according to the aspect 12, for forming a thermochromic laminate member capable of reversible change from a metallic luster color to a dye or pigment color, wherein the thermochromic sheet comprises, in addition to the thermochromic material, a non-thermochromic colored dye or pigment, and has a luminocity V1 of 6 or lower in the color-developed state and a luminocity V2 of 4 or higher in the color-extinguished state, wherein said luminocities satisfy a relation $V2-V1>1$.

14. Three combined sheets for forming a thermochromic laminate member capable of reversible change from a metallic luster color to a dye or pigment color, comprising:

A) a metallic luster sheet molded from a metallic luster pigment consisting of natural mica surfacially covered with titanium oxide and having a grain size of 5 to 100 μm, and synthetic resin;

B) a thermochromic sheet selected from (a) a sheet molded from a thermochromic material consisting of an electron donating compound, an electron accepting compound and an organic medium capable of causing a reversible color-forming reaction of said compounds and having a luminocity of 6 or lower in the color-generated state and a luminocity of 8 or higher in the colorless state, and (b) a sheet molded from a thermochromic material consisting of an electron donating compound, an electron accepting compound and an organic medium capable of causing a reversible color-forming reaction of said compounds and having a luminocity of 6 or lower in the color-generated state and a luminocity of 8 or higher in the colorless state, and a non-thermochromic colored dye or pigment, wherein the mixed system has a luminocity V1 of 6 or lower in the color-generated state and a luminocity V2 of 4 or higher in the color-diminished state, said luminocities satisfying a relation $V2-V1>1$; and C) a colored sheet composed of a non-thermochromic colored dye or pigment and synthetic resin, and having a luminocity V3 which satisfies a relation $V3-V4>1$, wherein V4 is the luminocity of the thermochromic material in the color-generated state.

15. Combined sheets according to any of the aspects 12 to 14, for forming a therochromic laminate member capable of reversible change from a metallic luster color to a colorless or pale yellow state or a dye or pigment color, wherein the thermochromic material consists of microcopsules enclosing an electron donating compound, an electron accepting compound and an organic medium capable of causing a reversible color-forming reaction of said compounds.

16. A thermochromic laminate member according to any of the aspects 1 to 15, wherein the metallic luster pigment is selected from a gold luster pigment consisting of natural mica surfacially covered with titanium oxide of 41–44 wt. % with an optical thickness of 180–240 nm, and having a particle size of 5–60 μm, a gold luster pigment consisting of natural mica surfacially covered with titanium oxide of 30–48 wt. % with an optical thickness of 140–240 nm, and having a grain size of 5–60 μm, a gold luster pigment consisting of natural mica surfacially covered with titanium oxide of 30–48 wt. % and with a non-thermochromic colored pigment of 0.5–10 wt. %, with a combined optical thickness of 140–240 nm, and having a particle size of 5–60 μm, a silver luster pigment consisting of natural mica surfacially covered with titanium oxide of 16–39 wt. % with an optical thickness of 110–170 nm, and having a particle size of 5–100 m, and a metallic luster pigment consisting of natural mica surfacially covered with titanium oxide of 45–58 wt. % with an optical thickness of 245–415 nm, and having a particle size of 5–60 μm.

17. A thermochromic laminate member according to the aspect 16, wherein the metallic luster pigment is selected from a metallic luster pigment consisting of natural mica surfacially covered with titanium oxide of 45–58 wt. % and then with iron oxide of 4–10 wt. % with a combined optical thickness of 245–415 nm, and having a particle size of 5–60 μm, a metallic luster pigment consisting of natural mica surfacially covered with titanium oxide of 435–58 wt. % and then with a non-thermochromic colored dye or pigment of 0.5–10 wt. % with a combined optical thickness of 245–415 nm, and having a particle size of 5–60 μm, a metallic luster red pigment consisting of natural mica surfacially covered with titanium oxide of 45–47 wt. % with an optical thickness of 245–275 nm, a metallic luster purple pigment consisting of natural mica surfacially covered with titanium oxide of 48–50 wt. % with an optical thickness of 280–310 nm, a metallic luster blue pigment consisting of natural mica surfacially covered with titanium oxide of 51–54 wt. % with an optical thickness 315–350 nm, or a metallic luster green pigment consisting of natural mica surfacially covered with titanium oxide of 55–58 wt. % with an optical thickness of 375–415 nm.

The metallic luster pigment, to be employed in the present invention, is a gold, silver or other metallic luster pigment, as will be explained in the folloiwng.

The gold luster pigment can be example be a gold luster pigment consisting of natural mica particles of which surface is covered with titanium oxide, a gold luster pigment consisting of natural mica particles of which surface is covered with titanium oxide and then with iron oxide, or a dichroic gold luster pigment in which said titanium oxide coating is covered with a non-thermochromic colored dye or pigment.

More specifically, the gold luster pigment can be a gold luster pigment consisting of natural mica particles of which surface is covered with titanium oxide of 41–44 wt. % with an optical thickness of 180–240 nm, and having a particle size of 5–60 μm, a metallic luster pigment consisting of natural mica particles of which surface is covered with titanium oxide of 30–48 wt. % and then with iron oxide of 4–10 wt. % with a combined optical thickness of 140–240 nm, and having a particle size of 5–60 μm, or a dichroic gold luster pigment consisting of natural mica particles of which surface is covered with titanium oxide of 30–48 wt. % and then with a non-thermochromic colored dye or pigment of 0.5–10 wt. % with a combined optical thickness of 140–240 nm, and having a particle size of 5–60 μm. The gold luster pigment can exhibit gold color within the numerical ranges mentioned above, by selectively transmitting the light of wavelength of purple color and reflecting the light of wavelength of complementary yellow color. Outside said ranges, the pigment either loses the selective absorbing character or can no longer exhibit gold color even if the selective absorbing character remains.

Also the gold luster pigment consisting of natural mica particles surfacially covered with titanium oxide and further covered with iron oxide has, in addition to the above-mentioned selective spectral reflection and transmission, the property of iron oxide itself of absorbing the purple light and reflecting the yellow light, thereby exhibiting a reversible change from more vivid gold color to pale yellow color. Since the coating layer is colored pale yellow because of the color of iron oxide itself, it appears pale yellow even if the background is white. If the coating amount of titanium oxide is less than 30 wt. %, sufficient gold color can only be obtained by increasing the coating amount of iron oxide in excess of 10 wt. %, but, in such case the metallic luster layer always exhibits gold color, so that a clear color change is not exhibited by the color change of the thermochromic material. Also if the coating amount of titanium oxide exceeds 48 wt. %, the selectively reflected light is no longer yellow, so that clear gold color cannot be obtained even if a coating with iron oxide is provided thereon. Also the above-mentioned effect of iron oxide cannot be obtained when the coating amount thereof is less than 4 wt. %. On the other hand, in case the coating amount of iron oxide exceeds 10 wt. %, there is obtained gold color, but the metallic luster layer always appears gold color and a clear color change cannot be obtained by the color change of the thermochromic material.

In case iron oxide is used in combination, it is most effective, for obtaining gold luster color, to form an iron oxide film on a titanium oxide coating. If the titanium oxide layer is fomred on the iron oxide layer, the effect of iron oxide will be reduced because of the strong reflective effect of titanium oxide. Also if titanium oxide and iron oxide are present in mixed state, the reflection efficiency of iron oxide becomes lower than in the structure with upper iron oxide layer, because the reflected light from iron oxide will be partially intercepted by titanium oxide.

If the iron oxide layer, having the property of absorbing purple light and reflecting other lights which appear as yellow, is provided on the titanium oxide layer, it provides an effect of deepening the gold luster color obtained by the titanium oxide layer, because the reflected light from such upper iron oxide layer is not intercepted by any other layer.

Also the gold luster pigment consisting of natural mica particles surfacially coated with titanium oxide and further with a non-thermochromic colored dye or pigment can exhibit more variable color changes, depending on the color of such non-thermochromic dye or pigment. For example, in combination with a black-white thermochromic layer, there can be exhibited a reversible change between gold color and a colored state, such as between gold color and pink color, or between gold color and blue color. If the coating amount of titanium oxide is less than 30 wt. %, it is difficult to obtain sufficient gold color, and gold color cannot be obtained if the non-thermochromic colored dye or pigment is coated, Also if said coating amount exceeds 48 wt. %, gold color cannot be obtained since the selectively reflected light is no longer yellow. If the coating amount of the non-thermochromic colored dye or pigment is less than 0.5 wt. %, the colored state cannot be obtained with a sufficient density. Also if said coating amount exceeds 10 wt. %, the gold color cannot be exhibited because the density of the colored state is too high. Therefore, within the aforementioned ranges, the pigment can have the propery of selectively transmitting the light of wavelength of gold color and reflecting the light of wavelength of complementary color. Outside said ranges, it either loses the spectral selectivity, or does not exhibit gold color even if the spectral selectivity is retained.

Also a thermochromic layer containing a coloring material consisting of a non-thermochromic dye or pigment exhibits a reversible change from gold luster color to the color of said coloring material. Since the gold luster pigment layer is translucent, the color of a non-thermochromic coloring layer placed thereunder can be exhibited simultaneously with the thermal color variation of the thermochromic layer. Also the characters or patterns in the underlying non-thermochromic coloring layer can be concealed in the colored state of the thermochromic layer, but the concealing effect can be enhanced by the light reflecting effect of the gold luster pigment layer, in comparison with the concealing effect solely by thermal color change.

In the present invention, the optical thickness of the coating layer means the refractive index times the geometrical thickness, and is related with the reflection of a certain wavelength. More specifically, a certain optical thickness causes the reflection of a certain light, and a titanium oxide coating layer formed, on the surface of natural mica, with a thickness of 180–240 nm reflects the light of gold color in the spectral region of 550–600 nm.

The silver luster pigment consists of natural mica particles surfacially coated with titanium oxide of 16–39 wt. %, with an optical thickness of said coating layer of 110–170 nm, and with a particle size of 5–100 $\mu$m. The above-mentioned numerical ranges prevent the spectral selectivity in the reflected light. Outside said ranges, the reflected light shows spectral selectivity, thus being colored and not appearing as silver. The titanium oxide layer of the above-mentioned optical characteristics reflects the light of silver color in the spectral range of 380–700 nm.

The thermochromic layer containing a coloring material consisting of a non-thermochromic dye pigment can exhibit a reversible change from the silver luster color to the colored state of the coloring material. Since the silver luster pigment layer is translucent, the color of a non-thermochromic coloring layer placed thereunder can be exhibited simultaneously with the thermal color variation of the thermochromic layer. Also the characters or patterns in the underlying non-thermochromic coloring layer can be concealed in the colored state of the thermochromic layer, but the concealing effect can be enhanced by the light reflecting effect of the silver luster pigment layer, in comparison with the concealing effect solely by thermal color change.

The metallic luster pigment to be employed in the present invention consists of natural mica particles surfacially coated with titanium oxide and has a metallic luster color. An iron oxide coating may also be provided on the titanium oxide layer. Also there may be employed a dichromatic metallic luster pigment in which the titanium oxide coating is covered with a non-thermochromic colored dye or pigment.

More specifically, said metallic luster pigment consists of natural mica particles which are surfacially coated with titanium oxide of 45–58 wt. %, with an optical thickness of the coating layer of 245–415 nm, and have as particle size of 5–60 $\mu$m, or natural mica particles which are surfacially coated with titanium oxide of 45-58 wt. % and further with iron oxide of 4-10 wt. %, with an optical thickness of the coating layers of 245-415 nm, and have a particle size of 5-60 μm. There can also be employed a dichroic metallic luster pigment consisting of natural mica particles surfacially coated with titanium oxide of 45-58 wt. % and further with a non-thermochromic colored dye or pigment of 0.5-10 wt. %, with an optical thickness of the coating layers of 245-415 nm and with a particle size of 5-60 μm.

The mica coated with titanium oxide has the function of reflecting the light of a particular wavelength, among the visible spectral range from red to purple, and reflecting other lights, depending on the coating weight and optical thickness of titanium oxide. On the other hand, the reflected light bears metallic luster, because mica does not cause random scattering but reflects light in parallel state. The light transmitted by the first layer is absorbed by the second thermochromic layer. A particular metallic color can be exhibited because the light of a specified wavelength with metallic luster is thus reflected.

Also the metallic luster pigment, consisting of natural mica particles surfacially coated with titanium oxide and further with iron oxide exhibits reversible change from a metallic luster color to pale yellow color, because the property of iron oxide for absorbing violet light and reflecting yellow light is added to the above-mentioned selective spectral reflection and transmission.

If the coating amount of titanium oxide exceeds 58 wt. %, the metallic luster color cannot be obtained because of the deteriorated spectral selectivity. Also a coating amount of iron oxide less than 4 wt. % does not provide sufficient effect of iron oxide mentioned above, and a coating amount exceeding 10 wt. % provides a metallic luster color but does not provide a clear color change from the metallic luster color because the color of iron oxide is excessively strong.

In case iron oxide is used in combination, it is most effective to form the iron oxide film on the titanium oxide film, in order to obtain the change from the metallic luster color to pale yellow color. If titanium oxide is coated on iron oxide, the effect thereof will be reduced because of the high reflecting efficiency of titanium oxide.

Also in case iron oxide and titanium oxide are present in mixed manner, the reflection efficiency of iron oxide becomes lower, in comparison with the structure containing the iron oxide in the upper layer, because the reflected light from iron oxide is partially intercepted.

If the iron oxide layer, having the property of absorbing violet light and reflected other lights which appear as yellow, is provided on the titanium oxide layer, it provides a color change from the metallic luster color, obtained by the titanium oxide layer, to pale yellow color, because the reflected light from such upper iron oxide layer not intercepted nor absorbed by any other layer.

Also the metallic luster pigment consisting of natural mica particles surfacially coated with titanium oxide and further with a non-thermochromic colored dye or pigment can exhibit more diversified color changes, depending on the color of such non-thermochromic dye or pigment. For example, in combination with a black-white thermochromic layer, there can be exhibited a reversible change between a metallic luster color and a colored state, for example between a metallic luster color and pink color or between a metallic luster color and blue color. If the coating amount of titanium oxide is less than 45 wt. %, metallic luster color is difficult to obtain in sufficient manner, and cannot be obtained if the non-thermochromic colored dye or pigment is coated. Also if said coating amount exceeds 58 wt. %, sufficient metallic luster color cannot be obtained because of the deteriorated spectral selectivity.

If the coating amount of the non-thermochromic colored dye or pigment is less than 0.5 wt. %, the colored state cannot be obtained with a sufficient density, and if said coating amount exceeds 10 wt. %, the contrast between the metallic luster color and the colored state becomes smaller because the density of said colored state is excessively high.

Therefore, within the above-mentioned ranges, the pigment can have the property of selectively transmitting the light of wavelength of metallic luster and reflecting the light of wavelength of complementary color. Outside said ranges, it either loses the spectral selectivity, or does not exhibit the metallic luster color even if the spectral selectivity is retained.

Also a thermochromic layer containing a coloring material consisting of a non-thermochromic dye or pigment exhibits a reversible change from the metallic luster color to the color of said coloring material. Since the metallic luster pigment layer is translucent, the color of a non-thermochromic coloring layer placed thereunder can be exhibited simultaneously with the thermal color variation of the thermochromic layer. Also the characters or patterns in the underlying non-thermochromic coloring layer can be concealed in the colored state of the thermochromic layer, and the concealing effect can be enhanced by the light reflecting effect of the metallic luster pigment layer, in comparison with the concealing effect solely by thermal color change.

The thermochromic layer is based on a thermochromic material containing an electron donating color-forming compound, an electron accepting compound, and an organic medium capable of causing a reversible color-forming reaction of said compounds. Examples of such thermochromic material include those disclosed in the aforementioned Japanese Patent Publication No. 51-35414, such as:

(1) a reversible thermochromic material essentially composed of (a) an electron donating color-forming organic compound, (b) a compound having a phenolic hydroxyl radical, and (c) an aliphatic straight-chain monohydroxylic alcohol without polar substituent;

(2) a reversible thermochromic material essentially composed of (a) an electron donating color-forming organic compound, (b) a compound having a phenolic hydroxyl radical, and (c) a compound selected from esters obtained from aliphatic monohydroxylic alcohols without polar substituent and aliphatic monocarboxylic acids without polar substituent;

(3) a reversible thermochromic material essentially composed of (a) an electron donating color-forming organic compound, (b) a compound having a phenolic hydroxyl radical, and (c) a compound selected from a group consisting of a higher aliphatic monohydroxylic alcohol without polar substituent, and an ester without polar substituent obtained from an aliphatic monocarboxylic acid without polar substituent and an aliphatic straight-chain monohydroxylic alcohol without polar substituent, and contained in microcapsules; and (4) a thermochromic material essentially composed of (a) an electron donating color-forming organic compound, (b) a compound having a phenolic hydroxyl radical, and (c) a compound selected from a group consisting of a higher aliphatic monohydroxylic alcohol without polar substituent, and an ester without polar substituent obtained from a higher aliphatic monocarboxylic acid without polar substituent and an aliphatic straight-chain monohydroxylic alcohol without polar substituent, and dissolved or dispersed in a vehicle.

The thermochromic material is most preferably contained in microcapsules, because it is maintained in a same composition and can exhibit constant effect under different conditions of use.

Also there can be employed a thermochromic material containing a color-memorizing thermochromic compound with a large hysteresis as disclosed in the U.S. Pat. No. 4,720,301. In such compound, the curve indicating the change of color density as a function of temperature is significantly different in case of temperature elevation from a lower temperature to the color-varying temperature region and in case of temperature lowering from a higher temperature to said color-varying temperature region, and, the state varied below the color-varying point of the lower temperature side or above the color-varying point of the higher temperature side can be retained at the normal temperature range.

The thermochromic laminate member of the present invention is composed of the aforementioned gold, silver or other metallic luster pigment and the thermochromic material, combined in layers of transparent film forming material.

Examples of said film forming material include ionomer resin, isobutyrene-maleic anhydride copolymer resin, acrylonitrile-acrylic styrene copolymer resin, acrylonitrile-styrene copolymer resin, acrylonitrile-butadiene-stryrene copolymer resin, acrylonitrile-butadiene-styrene copolymer resin, acrylonitrile-polyethylene chloride-styrene copolymer resin, ethylene-vinyl chloride copolymer resin, ethylene-vinyl acetate copolymer resin, ethylene-vinyl chloride graft polymer resin, vinylidene chloride resin, vinyl chloride resin, chlorinated vinyl chloride resin, vinyl chloride-vinylidene chloride copolymer resin, chlorinated polyethylene resin, chlorinated polypropylene resin, polyamide resin, high-density polyethylene resin, medium or low density polyethylene resin, low-density linear polyethylene resin, polyethylene terephthalate resin, polybutyrene terephthalate resin, polycarbonate resin, polypropylene resin, high-impact polystyrene resin, polypropylene resin, polymethylstyrene resin, polyacrylic ester resin, polymethylmethacrylate resin, epoxyacrylate resin, alkylphenol resin, rosin-denatured phenolic resin, rosin-denatured alkyd resin, phenolic resin-denatured alkyd resin, epoxy resin-denatured alkyd resin, styrene-denatured alkyd resin, acrylate-denatured alkyd resin, aminoalkyd resin, vinyl chloride-vinyl acetate resin, styrene-butadiene resin, epoxy resin, unsaturated polyester resin, polyurethane resin, vinyl acetate emulsion resin, styrene-butadiene emulsion resin, acrylic ester emulsion resin, water-soluble alkyd resin, water-soluble melamine resin, water-soluble urea resin, water-soluble phenolic resin, water-soluble epoxy resin, water-soluble polybutadiene resin, and cellulose derivatives such as cellulose acetate, cellulose nitrate and ethyl cellulose.

In the present invention, the above-mentioned resins are collectively called synthetic resins, and the film forming materail is suitably selected from said resins according to the purpose.

Each of the layers of the thermochromic laminate member of the present invention may be formed by applying a coating composition.

Said coating composition is composed of the above-mentioned film forming material, such as alkylphenol resin, rosin-denatured phenolic resin, resin-denatured alkyd resin, phenolic resin-denatured alkyd resin, epoxy resin-denatured alkyd resin, styrene-denatured alkyd resin, acrylae-denatured alkyd resin, aminoalkyd resin, vinyl chloride-vinyl acetate resin, styrene-butadiene resin, epoxy resin, acrylic ester resin, unsaturated polyester resin, polyurethane resin, vinyl acetate emulsion resin, styrene-butadiene emulsion resin, acrylic ester emulsion resin, water-soluble alkyd resin, water-soluble melamine resin, water-soluble urea resin, water-soluble phenolic resin, water-soluble epoxy resin, water-soluble polybutadiene resin or cellulose derivative, dissolved or dispersed in a vehicle such as water or organic solvent.

Also each of the layers of the thermochromic laminate member of the present invention may be composed of a molded sheet, containing the pigment or the thermochromic material in synthetic resin.

In such sheet there is employed the above-mentioned film forming material such as ionomer resin, isobutyrene-maleic anhydride copolymer resin, acrylonitrile-acrylic styrene copolymer resin, acrylonitrile-styrene copolymer resin, acrylonitrile-butadiene-styrene copolymer resin, acrylonitrile-chlorinated polyethylene-styrene copolymer resin, ethylene-vinyl chloride copolymer resin, ethylene-vinylidene acetate copolymer resin, ethylene-vinyl acetate-vinyl chloride graft copolymer resin, vinylidene chloride resin, vinyl chloride resin, chlorinated vinyl chloride resin, vinyl chloride-vinylidene chloride copolymer resin, chlorinated polyethylene resin, chlorinated polypropylene resin, polyamide resin, high-density polyethylene resin; middle- or low-density polyethylene resin, linear low-density polyethylene resin, polyethylene terephthalate resin, polybutyrene terephthalate resin, polycarbonate resin, polystyrene resin, high-impact polyetyrene resin, polypropylene resin, polymethylstyrene resin, polyacrylic ester resin, polymethylmethacrylate resin, epoxy resin epoxyacrylate resin, alkyd resin or polyurethane resin.

The laminate member may be prepared by the combination of sheets and coated films.

The metallic luster pigment layer preferably employs transparent resin.

The laminate member may be formed on the surface of a substrate, or formed as an independent article without substrate.

The substrate can not only be a film or a sheet of various kinds, but also be the surface of a molded article. Thus the thermochromic laminate member can be formed on the surface of a molded article to obtain a thermochromic molded article. Examples of such substrate include paper, synthetic paper, cloth, non-woven cloth, leather, synthetic leather, plastics, glass, ceramics, metal, wood and stone. Also the substrate need not necessarily be flat but can have ban ondular or fiber-shaped surface.

The laminate member can be formed by a knwon method of printing, such as screen printing, offset printing, gravure printing, tampon printing or transfer printing, or coating such as brush coating, spray coating, electrostatic coating, electrodeposition coating, flow coating, roller coating or immersion coating. It can also be obtained by adhering a film sheet formed by extrusion molding, or by multi-layer molding of the thermochromic layer and the metallic luster pigment layer.

Furthermore, if necessary, each of the metallic luster pigment layer and the thermochromic layer may be added with an additive or additives, such as ultraviolet absorbing agent, infrared absorbing agent, antioxidant, singlet oxygen quencher, antiaging agent, antistatic agent, polarity enhancing agent, thixotropy providing agent, defoamer, stabilizer, plasticizer, flame retardant, lubricant and foaming agent.

The thermochromic laminate member of the present invention, including a metallic luster pigment layer of gold, silver or other metallic color laminated on a thermochromic layer, allows the user to observe the color change in said thermochromic layer through said metallic luster pigment layer, there can be demonstrated various color changes involving metallic luster, through the multiplying effect of the coloring and transmission, resulting from the selective interference of the visible wavelength region depending on the coating weight and optical thickness of titanium oxide on the natural mica particles, and of the reflection and absorption of the thermochromic layer on the luminocity of the visible light. More specifically, the mica varies the wavelength of the reflected light, depending on the coating amount, or the thickness, of the titanium oxide coating. For example, mica, coated with titanium oxide with an optical thickness of 180–240 nm so as to selectively reflect the yellow light and transmit the violet light, appears as gold color in case the underlying layer is black, since the transmitted violet light is absorbed by the underlying black layer and the yellow light of 550–600 nm alone is reflected. On the other hand, if the underlying layer is white, the transmitted violet light is also reflected by said underlying layer. Thus it appears as white, as all the visible spectral region is reflected. Therefore, by a reversible change between black and white in the underlying thermochromic layer, the observer can observe a reversible color change between gold and white.

If the optical thickness is outside the above-mentioned range, the gold color is not exhibited since the reflected light is not within the wavelength range of 550–600 nm.

In the system in which the metallic luster pigment layer of silver color is laminated on the thermochromic layer, the user observes the color change of the thermochromic layer through the metallic luster pigment layer of silver color. As explained above, white color is observed when all the visible light is reflected. If a part of the entering light is reflected over the entire spectral range and the remainder is reflected, the reflected light becomes darker and appears as gray.

Since mica has a laminar structure, the reflection does not take place randomly but in a same direction. Such reflected light is felt as metallic luster. The gray color bearing metallic luster appears as silver. In this manner silver color with metallic luster is exhibited.

It is essential that the optical thickness of titanium oxide is within a range of 110–170 nm.

Outside said range, the reflected light has spectral selectivity, thus being colored and no longer appearing as silver color.

The system including the metallic luster pigment layer laminated on the thermochromic layer allows the user to observe the color change of said thermochromic layer through the metallic luster pigment layer. As explained above, the mica coated with titanium oxide has a function of reflecting the light of a particular wavelength among the visible region from red to violet and transmitting the lights of other wavelengths, depending on the coating weight and optical thickness of titanium oxide. Also the reflected light bears metallic luster since the mica does not reflect the light randomly but in parallel state. The light transmitted by the first layer is absorbed in the second thermochromic layer. In this manner the light with metallic luster of a particular wavelength is reflected to demonstrate a particular metallic luster color. More specifically, the mica varied the wavelength of the reflected light, depending on the coating amount, or the optical thickness, of the titanium oxide coating. For example, mica, coated with titanium oxide of an optical thickness so as to selectively reflect the light of a specified color and transmit the lights of other colors, appears as said specified color with metallic luster, since the transmitted lights are absorbed by a black underlying layer and the light of said specified color along is reflected. On the other hand, if the underlying layer is white, it appears as white since the transmitted light is also reflected by said white underlying layer, so that the entire visible spectral range is reflected. Therefore, by a reversible change between black and white in the underlying thermochromic layer, there can be observed a reversible change between the specified metallic luster color and white.

It is essential that the optical thickness of titanium oxide is within a range of 245–415 nm.

If the optical thickness of titanium oxide, coated on natural mica, is within the above-mentioned range, the reflected light is separated in the region of red to violet depending on said optical thickness, and in parallel state, thus appearing as a metallic luster color.

For example, a pigment with a coating amount of titanium oxide of 45–47 wt. % and with an optical thickness of 245–275 nm transmits the green light of 500–550 nm and reflects the red light of 650–700 nm. When the light transmitted by said pigment layer is absorbed by the underlying thermochromic layer, the observer can only observe the red color with metallic luster.

When the light transmitted by the metallic luster pigment layer is reflected by the thermochromic layer, the observer perceives white color as the entire visible spectral region is reflected. Thus, the metallic luster color appears and disappears reversibly, by a change in luminocity caused by the color change in the thermochromic layer. Since the mica particles are arranged in parallel layers, the reflection does not take place randomly but in parallel state, and such parallel reflected light bears metallic luster. Consequently the reflected light from said pigment appears as red color with metallic luster.

Similarly a pigment with a coating amount of titanium oxide of 55–58 wt. % and with an optical thickness 375–415 nm transmits the red light of 630–700 nm and reflects the green light of 500–540 nm, thus appearing as green color with metallic luster.

Also a pigment with a coating amount of titanium oxide of 51–54 wt. % and with an optical thickness of 315–350 nm transmits the orange light of 580–630 nm and reflects the blue light of 430–500 nm, thus appearing as blue color with metallic luster.

Also a pigment with a coating amount of titanium oxide of 48–50 wt. % and with an optical thickness of 280–310 nm transmits the yellow light of 530–580 nm and reflects the violet light of 380–430 nm, thus appearing as violet color with metallic luster.

As explained in the foregoing, the present invention enables reflection of the light of a specified wavelength by a specified coating amount and a specified optical thickness of titanium oxide, and provides gold, silver or other metallic luster colors by the interference effect of mica and the colored-colorless change of the thermochromic material.

In the following there will be explained embodiments of the thermochromic laminate member of the present invention.

The present invention provides (A) a thermochromic laminate member in which a metallic luster pigment layer is laminated on a thermochromic layer, (B) a thermochromic laminate member in which a metallic luster pigment layer is laminated on a thermochromic layer containing a thermochromic material and a non-thermochromic dye or pigment, and (C) a metallic luster pigment is laminated on a thermochromic layer which is in turn laminated on a non-thermochromic colored layer.

Said thermochromic laminate member may be formed on a substrate, or may have a transparent protective film on said metallic luster pigment layer, or may have a clear coating or a transparent laminate layer between the thermochromic layer and the metallic luster pigment layer.

In the following, the above-mentioned embodiments (A)–(C) will be explained further.

In said embodiment (A), the metallic luster pigment layer is composed of a metallic luster pigment with a particle size of 5–100 μm dispersed in transparent resin, while the thermochromic layer is composed of a thermochromic material, consisting of a uniform solution of an electron donating color-forming organic compound, an electron accepting compound, and an organic medium capable of causing a reversible color-forming reaction of said compounds, and dispersed in a transparent film forming material, and has a luminocity of color density of 6 or lower in the color-developed state and a luminocity of 8 or higher in the color-extinguished state. Thus there is constituted a metallic luster thermochromic laminate member capable of reversible change between a metallic luster color and a colorless state.

If the luminocity of color density is 6 or lower in the color-developed state, the light transmitted by the upper metallic luster pigment layer can be satisfactorily abosrbed, so that, for example in case of a gold luster pigment, the gold luster color can be clearly perceived. On the other hand, if said luminocity exceeds 6, the light transmitted by the gold luster pigment cannot be sufficiently absorbed and is partly reflected again, so that the gold luster pigment cannot be sufficiently absorbed and is partly reflected again, so that the gold luster color cannot be perceived clearly. Also if the luminocity in the color-extinguished state is 8 or higher, the light transmitted by the gold luster pigment can be satisfactorily reflected, and white color perceived by the mixing of the light reflected by the gold luster pigment and the light reflected by the thermochromic material. On the other hand, if said luminocity is less than 8, the light transimtted by the gold luster pigment cannot be sufficiently reflected but partly absorbed, so that the colorless state cannot be attained and the gold luster color in the color-developed state remains.

In said embodiment (B), the metallic luster pigment layer is composed of a metallic luster pigment with a particle size of 5–100 μm dispersed in transparent resin, while the thermochromic layer contains the aforementioned thermochromic material and a non-thermochromic coloring material such as a dye or a pigment, and has a luminocity V1 of color density of 6 or lower in the color-developed state and a luminocity V2 of 4 or higher in the color-diminished state, and further satisfies a relation $V2-V1>1$. Thus there is constituted a metallic luster thermochromic laminate member capable of reversible change between a metallic luster color and a colored state.

The luminocity V1 of the color density of the mixture has to be 6 or lower in the color-developed state, for the same reason as explained above.

On the other hand, the luminocity V2 of the mixture has to be 4 or higher in the color-diminished state and a condition $V2-V1>1$ has to be satisfied, because of the following reason. Because this system is colored by the presence of the non-thermochromic dye or pigment, the luminocity becomes smaller and varies according to the color of said dye or pigment. For example, the luminocity is relatively large for yellow or orange color, but becomes smaller for red or violet. However, in order to obtain a satisfactory color change, the luminocity in the color-diminished state should be larger, at least larger than by 1, than that in the color-developed state. If the difference in luminocity is 1 or less, the color changes is not clear because of excessively small contrast. Under such condition, a luminocity of 4 or larger can provide a reversible change for example between gold color and a colored state. On the other hand, if the luminocity is less than 4, the underlying mixture layer has an excessively high color density, thus absorbing the transmitted light, so that the gold luster color can be perceived even in the color-diminished state.

In the embodiment (C), under the therochromic layer, there is formed a non-thermochromic colored layer, having a luminocity V3 of color density of 4 or higher and satisfying a relation $V3-V4>1$, wherein V4 is the luminocity of the thermochromic layer in the color-developed state. Thus there is constituted a metallic luster thermochromic laminate member capable of reversible change between a metallic luster color and the color of said non-thermochromic colored layer.

The above-mentioned luminocity in the color developed or color-diminished state of the thermochromic material is represented by the luminocity value in the Munsell color system, in which complete black and white are respectively represented by 0 and 10, and the scale therebetween is so divided as to provide an equal difference in the perceived brightness, and the luminocity of any color corresponds to that of colorless luminocity which is equal in the perceived brightness of said color. The luminocity value, being smaller or larger as the color is closer to black or white, can be utilized as a index indicating the extent of absorption and reflection of the visible light. Said index indicates the level of reflection and absorption, by the underlying thermochromic layer, on the light transmitted by the metallic luster pigment layer.

The thermochromic layer, having a luminocity of 6 or less, is capable of sufficiently absorbing the light transmitted by the metallic luster pigment layer. As a result, the laminate member appears as gold color since only the yellow light, reflected by said metallic luster pigment layer, can be perceived. On the other hand, if the luminocity is 8 or higher, the visible light transmitted by the metallic luster pigment layer is reflected and is perceived together with the yellow light reflected by the metallic luster pigment layer, so that the metallic luster color can no longer be perceived.

Therefore, the above-mentioned luminocity values are indexes for the laminate member to show a metallic luster color below the color-changing temperature of the thermochromic material and to lose such metallic luster color above said color-changing temperature. The luminocity in the present invention was determined with a color difference meter TC-3600 manufactured by Tokyo Denshoku Co., Ltd., on samples prepared in the following manner:

1. Thermochromic layer (including systems containing ordinary dye or pigment):
    (1) Thermochromic layer (colored-colorless)
    10 parts of thermochromic mateiral, 45 parts of 50% solution of acrylic ester resin in xylene, 20 parts of zylene and 20 parts of methylisobutylketone are mixed under agitation, and spray coated with a spray gun on a white polyvinyl chloride sheet with a luminocity of 9.1 to obtain a thermochromic layer with a dried thickness of 40 μm. The luminocities of thus obtained thermochromic layer are measured in the color-devleoped state and color-extinguished state.
    (2) Thermochromic layer (colored I—colored II)
    10 parts of thermochromic material, a desired amount of an ordinary dye or pigment, 45 parts of 50 solution of acrylic ester resin in xylene, 20 parts of xylene and 20 parts of methylisobutylketone are mixed under agitation and spray coated with a spary gun on a white polyvinyl chloride sheet with a luminocity of 9.1 to obtain a thermochrmoic layer with a dried thickness of 40 μm. The luminocities of thus obtained thermochromic layer are measured in the color-developed state and color-extinguished state.

2. Non-thermochromic Colored Layer (colored by ordinary dye or pigment)

A desired amount of an ordinary dye or pigment, 45 parts of 50% solution of acrylic ester resin in xylene, 20 parts of xylene and 20 parts of methylisobutylketon are mixed under agitation, and spray coated with a spray gun on a white polyvinyl chloride sheet with a luminocity of 9.1 thereby obtaining a non-thermochroic colored layer with a dried thickness of 10 μm. The luminocity of thus obtained layer is measured.

BRIEF DESCRIPTION OF THE DRAWINGS

FIGS. 4 to 9 illustrate applications of the thermochromic laminate member of the present invention, wherein FIG. 4 illustrates an example applied to a miniature car toy, FIG. 6 illustrates an example applied to an accessory, FIG. 8 illustrates an example to an artificial nail and FIGS. 5, 7 and 9 respectively show the color-varied state of said applications.

DETAILED DESCRIPTION OF THE PREFERRED EMBODIMENTS

In the following there will be explained examples of the first embodiment of the present invention, capable of showing color change from gold color. In the folloiwng examples, the amounts are represented by part by weight.

EXAMPLE 1

Figure 1:
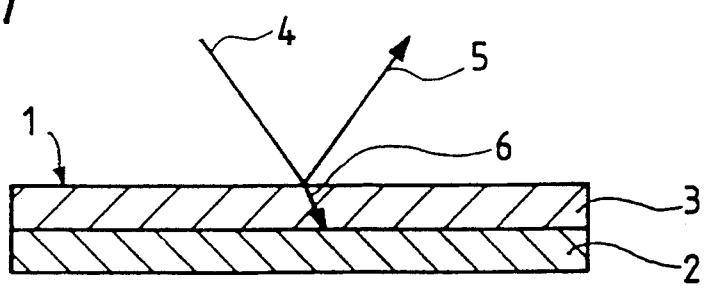
FIG. 1 is a schematic view of an embodiment of the thermochromic laminate member of the present invention.

FIG. 1 illustrates the example 1 of the present invention, consisting of a two-layered thermochromic laminate member 1. A first layer 3 of a thickness of about 40 μm, is composed of a gold luster pigment consisting of natural mica particles surfacially coated with titanium oxide of 43 wt. % with an optical thickness of 210 nm, and having a particle size of 10–60 μm, and acrylic ester resin, and said layer serves to regulate the wavelength of the reflected light.

There are also shown an incident light 4 and a reflected light 5. The non-reflected portion 6 of the incident light 4 is absorbed by a thermochromic layer 2.

The second thermochromic layer 2 of a thickness of about 40 μm was composed of a thermochromic material and acrylic ester resin. Said therochromic material consisted of microcapsules of an average particle size of 8 μm, formed by interfacial polymerization employing epoxy resin and an amine hardening agent, and enclosing solution of 3 parts of 2-anilino-3-methyl-6-dibutylaminofluorane, 6 parts of bisphenol-A and 50 parts of neopentyl stearate, and had luminocities of 2.2 and 9.0 respectively in the color-developed state and in the color-extinguished state, which were reversibly assumed by temperature change.

At 15° C. or lower, the thermochromic layer developed color to reflect the light 5 in a spectral region of 550–600 nm and to absorb the light 6 of other wavelengths, whereby the member appeared as gold luster color. At 30° C., the thermochromic layer lost color and reflects the transmitted light.

Since all the incident light was reflected in this manner, the gold luster color vanished and the element appeared colorless.

EXAMPLE 2

The example 1 was reproduced except the use of a thermochromic material which was similarly prepared with 1 part of 2-anilino-3-methyl-6-dibutylaminofluorane and 2 parts of 1,3-dimethyl-6-diethylaminofluorane instead of 2-anilino-3-methyl-6-dibutylaminofluorane in the example 1 and which showed luminocities of 2.7 and 8.8 respectively in the color-developed state and in the color-extinguished state. The member showed gold luster color at 15° C. or lower, and became colorless at 30° C. or higher.

EXAMPLE 3

The example 1 was reproduced except the use of a thermochromic material which was similarly prepared with 1.5 parts of 6-diethylamino-benzo(a)-fluorane instead of 2-anilino-3-methyl-6-dibutylaminofluorane in the example 1 and which showed luminocities of 4.0 and 8.9 respectively in the color-developed state and in the color-extinguished state. Similarly the member showed gold luster color at 15° C. or lower, and became colorless at 30° C. or higher.

EXAMPLE 4

The example 1 was reproduced except the use of a thermochromic material which was similarly prepared with 1.5 parts of 3-(4-diethylamino-2-ethoxyphenyl)-3-(1-ethyl-2-methylindol-3-yl)-4-azaphthalide instead of 2-anilino-3-methyl-6-dibutylaminofluorane in the example 1 and which showed luminocities of 3.2 and 8.7 respectively in the color-developed state and in the color-extinguished state. Similarly the member showed gold luster color at 15° C. or lower, and became colorless at 30° C. or higher.

EXAMPLE 5

The example 1 was reproduced except that the gold luster pigment in the example 1 was replaced by a gold luster pigment which consisted of natural mica surfacially coated with titanium oxide of 42 wt. % and further with Prussian blue of 2.5 wt. %, with an optical thickness of 210 nm, and had a particle size of 10–50 μm. The member showed gold luster color at 15° C. or lower, and became blue at 30° C. or higher.

EXAMPLE 6

Figure 2:
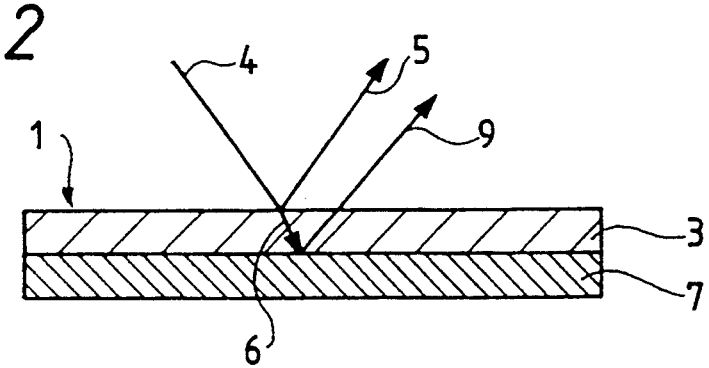
FIGS. 2 and 3 are schematic views showing other embodiments.

FIG. 2 shows another embodiment of the present invention, wherein a first layer 3 of a thickness of about 40 μm was composed of a gold luster pigment and acrylic ester resin, said pigment 1 consisting of natural mica surfacially coated with titanium oxide of 36 wt. % and further with ion oxide of 8 wt. %, with an optical thickness of 200 nm, and having a particle size of 10–60 μm. A second layer 7 of a thickness of about 40 μm was composed of the thermochromic material employed in the example 1, a non-thermochromic fluorescent yellow pigment and acrylic ester resin, and was capable of reversible change between a thermally color-developed state and a color-extinguished state with the color of said fluorescent yellow pigment, with luminocities of 2.5 and 8.9 respectively in the color-developed state and in the color-extinguished state.

At 15° C. or lower, the thermochromic layer developed color to reflect the light 5 of a spectral region of 550–600 nm in the incident light and to absorb the light 6 of other wavelengths whereby the member exhibited gold luster color. At 30° C. or higher, the thermochromic layer extinguished color, whereby the gold luster color disappeared and the color of the fluorescent yellow pigment was exhibited. A numeral 9 indicates the yellow light reflected by the thermochromic layer 7.

EXAMPLE 7

The metallic luster pigment layer 3 was same as that in the example 1. The thermochromic layer 7 of a thickness of about 40 μm was composed of the thermochromic material employed in the example 2, a fluorescent pink pigment and acrylic ester resin, and capable of reversible change between a thermally color-developed state and a color-extinguished state with the color of the fluorescent pink pigment, with luminocities of 2.3 and 5.5 respectively in the color-developed state and in the color-extinguished state.

At 15° C. or lower there was exhibited gold luster color, which was replaced by the color of the fluorescent pink pigment at 30° C. or higher. A numeral 9 indicates the pink light reflected by the thermochromic layer 7.

EXAMPLE 8

The metallic luster pigment layer 3 was same as that in the example 1. The thermochromic layer 7 of a thickness of about 40 μm was composed of the thermochromic material employed in the example 1, a fluorescent pink pigment, a blue pigment and acrylic ester resin, and capable of reversible change between a thermally color-developed state and a color-extinguished state with lavender color realized by the mixing of fluorescent pink and blue colors, with luminocities of 2.4 and 5.5 respectively in the color-developed state and in the color-extinguished state. Similarly, at 15° C. lower, there was exhibited gold luster color, which was replaced, at 30° C. or higher, by lavender color obtained by mixing of the fluorescent pink and blue pigments. A numeral 9 indicates the lavender-colored light reflected by the thermochromic layer 7.

EXAMPLE 9

The metallic luster pigment layer 3 was same as that in the example 1. The thermochromic layer 7 of a thickness of about 40 μm was composed of the thermochromic material employed in the example 1, a blue pigment, a white pigment and acrylic ester resin, and capable of reversible change between a thermally color-developed state and a color-extinguished state with pastel blue color which was the mixed color of the blue and white pigments, with luminocities of 2.2 and 5.4 respectively in the color-developed state and in the color-extinguished state. Similarly, at 15° C. or lower, there was exhibited gold luster color, which was replaced, at 30° C. or higher, by pastel blue color which was the mixed color of the blue and white pigments. A numeral 9 indicates the pastel blue-colored light reflected by the thermochromic layer 7.

EXAMPLE 10

Figure 3:
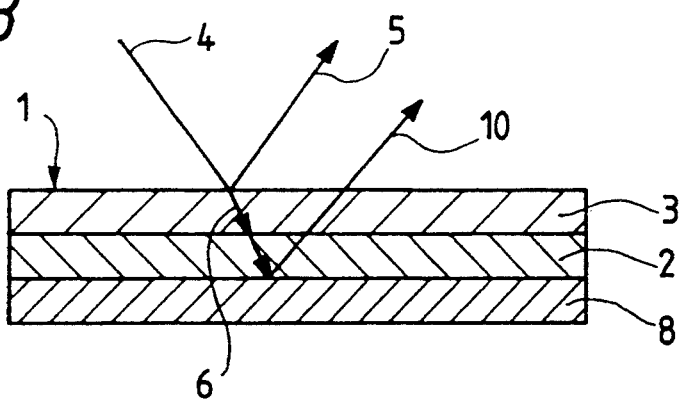

FIG. 3 shows another embodiment of the present invention, consisting of a three-layered thermochromic laminate member, comprising layers 2, 3 same as in the example 1 and a third colored layer 8, containing a non-thermochromic coloring material and positioned adjacent to the thermochromic layer 2. In this example, the colored layer 8 was fluorescent orange color and had a thickness of about 10 μm, composed of a fluorescent orange pigment and acrylic ester resin, with a luminocity of 6.3. At 15° C. or lower, the thermochromic layer developed color, whereby the light 5 of a spectral region of 550–600 nm in the incident light was reflected while the light 6 of other wavelengths was absorbed, thus exhibiting gold luster color. At 30° C. or higher, the color of the thermochromic layer was extinguished, whereby the gold luster color was replaced by the color of the underlying fluorescent orange color. A numeral 10 indicates the orange light reflected by the layer 8.

EXAMPLE 11

The example 10 was reproduced except that the fluorescent orange pigment in the colored layer 8 was replaced by a fluorescent red pigment with a luminocity of 4.7, and that the thermochromic layer was replaced by a layer of a thickness of about 40 μm composed of acrylic ester resin and a thermochromic material in the form of microcapsules of an average particle size of 8 μm, which were obtained by interfacial polymerization microencapsulation with epoxy resin and an amine hardening agent, enclosing a thermochromic composition consisting of 3 parts of 2-anilino-3-methyl-6-dibutylaminofluorane, 6 parts of bisphenol-A and 25 parts of cetyl caprate and which showed luminocities of 2.2 and 9.0 respectively in the color-developed state and in the color-extinguished state. At 20° C. or lower, the thermochromic layer developed color, whereby the light 5 of a spectral range of 550–600 nm in the incident light was reflected, while the light 6 of other wavelengths was absorbed, thus exhibiting gold luster color. At 20° C. or higher, the color of the thermochromic layer was extinguished, whereby the gold luster color was replaced by the color of the underlying fluorescent red pigment. A numeral 10 indicates the red light reflected by the layer 8.

EXAMPLE 12

The example 10 was reproduced except that, in the colored layer 8 of the example 11, the fluorescent orange pigment was replaced by a fluorescent pink pigment with a luminocity of 5.6. Similarly, below 20° C., the thermochromic layer developed color, whereby the light 5 in a spectral range of 550–600 nm in the incident light was reflected while the light 6 of other wavelength was absorbed, thus exhibitng the gold luster color. Above 20° C., the color of the thermochroic layer was extinguished, whereby the gold luster color was replaced by the color of the underlying fluorescent pink pigment. A numeral 10 indicates the pink light reflected by the layer 8.

EXAMPLE 13

The example 10 was reproduced except that, in the colored layer 8 of the example 11, the fluorescent orange pigment was replaced by a fluorescent green pigment with a luminocity of 8.2. Similarly the therochromic layer developed color below 20° C. whereby the light 5 of a spectral region of 550–600 nm in the incident light was reflected while the light 6 of other wavelengths was absorbed, thus exhibiting gold luster color. The color of the thermochromic layer was extinguished above 20° C., whereby the gold luster color was replaced by the color of the underlying fluorescent green color. A numeral 10 indicates the green light reflected by the layer 8.

Reference example 1

The example 1 was reproduced except that the thermochromic material therein was replaced by a thermochromic material in the form of microcapsules with an average particle size of 8 μm, which was obtained by interfacial polymerization microencapsulation with epoxy resin and an amine hardening agent, enclosing a thermochromic composition consisting of 6 parts of 2-anilino-3-methyl-6-dibutylaminofluorange, 10 parts of bisphenol-A and 25 parts of neopentyl stearate and not becoming colorless in the color-extinguished state, and which had luminocities of 4.5 and 6.0 respectively in the color-developed state and in the color-extinguished state. The thermochromic layer developed color at 15° C. or lower, whereby the light 5 of a spectral region of 550–600 nm in the incident light was reflected, while the light 6 of other wavelengths, thus exhibiting gold luster color. However, in this reference example, even when the color of the thermochromic layer was diminished at 30° C. or higher, it could still sufficiently absorb the transmitted light 6, so that the gold luster color became somewhat thinner but could still be perceived.

Reference example 2

The example 6 was reproduced except that the fluorescent yellow pigment therein was replaced by a blue pigment showing luminocities of 2.5 and 3.3 in the mixture respectively in the color-developed state and in the color-extinguished state, and that the thermochromic layer of a thickness of about 40 μm was composed of the thermochromic material of the example 1, the blue pigment and acrylic ester resin. The thermochromic layer developed color similarly at 15° C. or lwoer, whereby the light 5 of a spectral region of 550–600 nm in the incident light was reflected, while the light 6 of other wavelengths was absorbed, thus exhibiting gold luster color. In this reference example, however, as the thermochromic layer was sufficiently capable of absorbing the transmitted light 6 in its color-extinguished state at 30° C. or higher, the exhibited color merely changed to bluish gold and still bore gold luster.

Reference example 3

The example 10 was reproduced except that the fluorescent orange pigment therein was replaced by a red pigment whereby the colored layer 8 was a red pigment layer with a luminocity of 3.7. The thermochromic layer similarly developed color at 15° C. or lower, whereby the light 5 of a spectral region of 550–600 nm in the incident light was reflected while the light 6 of other wavelengths was absorbed, thus exhibiting gold luster color. In this reference example, however, since the thermochromic layer was still capable of sufficiently absorbing the transmitted light 6 even in the extinguished state at 30° C. or higher, the exhibited color merely changed to reddish gold and still showed gold luster.

In the following there will be explained example 5 of color change from silver luster color, with reference to the attached drawings.

EXAMPLE 1

FIG. 1 illustrates the example 1, consisting of a two-layered thermochromic laminate member 1. A first layer 3 of a thickness of about 40 μm, was composed of silver luster pigment consisting of natural mica particles surfacially coated with titanium oxide of 29 wt % with an optical thickness of 140 nm, and having a particle size of 10–60 μm, and acrylic ester resin, and said layer serves to regulate the wavelength of the reflected light.

There are also shown an incident light 4 and a reflected light 5. The non-reflected portion 6 of the incident light 4 is absorbed by a thermochromic layer 2.

A second thermochromic layer 2 of a thickness of about 40 μm was composed of a thermochromic material and acrylic ester resin. Said thermochromic material A consisted of microcapsules of an average particle size of 8 μm, formed by interfacial polymerization microencapsulation employing epoxy regin and an amine hardening agent, and enclosing solution of 3 parts of 2-anilino-3-methyl-6-dibutylaminofluorane, 6 parts of bisphenol-A and 50 parts of neopentyl stearate, and had luminocities of 2.2 and 9.0 respectively in the color-developed state and in the color-extinguished state, which were reversibly assumed by temperature change.

The thermochromic layer developed color at 15° C. or lower whereby the light 5 constituting a part of the incident visible light was reflected while the light 6 of other wavelengths, thus providing silver luster color. The thermochromic layer lost color at 30° C. to reflect the transmitted light 6, whereby all the incident light was thus reflected and the silver luster color was changed to colorless state.

EXAMPLE 2

The example 1 was reproduced except the use of a thermochromic material B showing luminocities of 2.7 and 8.8 respectively in the color-developed state and in the color-extinguished state, and prepared similarly by replacing 2-anilino-3-methyl-6-dibutylfluorane in the example 1 with 1 part thereof and 2 parts of 1,3-dimethyl-6-diethylaminofluorane. Similarly, at 15° C. or lower, there was exhibited silver luster color, which was replaced by a colorless state at 30° C. or higher.

EXAMPLE 3

The example 1 was reproduced except the use of a thermochromic material C showing luminocities of 3.0 and 8.7 respectively in the color-developed state and in the color-extinguished state, and prepared similarly by replacing 2-anilino-3-methyl-6-dibutylfluorane in the example 1 with 2.5 parts of 2-N,N-dibenzylamino-6-diethylaminofluorane. Similarly, at 15° C. or lower, there was exhibited silver luster color, which was replaced by a colorless state at 30° C. or higher.

EXAMPLE 4

The example 1 was reproduced except the use of a thermochromic material D showing luminocities of 3.2 and 8.7 respectively in the color-developed state and in the color-extinguished state, and prepared similarly by replacing 2-anilino-3-methyl-6-dibutylfluorane in the example 1 with 1.5 parts of 3-(4-diethylamino-2-ethoxyphenyl)-3-(1-ethyl-2-methylindol-3-yl)-4-azaphthalide. Similarly, at 15° C. or lower there was exhibited silver luster color, which was replaced by a colorless state at 30° C. or higher.

EXAMPLE 5

The example 1 was reproduced except that the silver luster pigment in the example 1 was replaced by a silver luster pigment having a particle size of 5-20 μm and consisting of natural mica particles surfacially coated with titanium oxide of 38 wt. % with an optical thickness of 160 nm. Similarly at 15° C. or lower there was exhibited silver luster color, which was replaced by a colorless state at 30° C. or higher.

EXAMPLE 6

FIG. 2 shows another embodiment of the present invention, wherein a first layer 3 was same as that in the example 1. A second thermochromic layer 7 of a thickness of about 40 μm was composed of the thermochromic material employed in the example 1, a non-thermochromic fluorescent yellow pigment, and acrylic ester resin, and was capable of reversible change between a thermally color-developed state and a color-extinguished state with the color of said luorescent yellow pigment, with luminocities of 2.5 and 8.9 respectively in the color-developed state and in the color-extinguished state.

The thermochromic layer developed color at 15° C. or lower, whereby the light 5 constituting a part of the incident visible light while the light 6 of other wavelength is absorbed, thus exhibiting silver luster color. At 30° C. or higher, the color of the thermochromic layer was extinguished, whereby the silver luster color was replaced by the color of the fluorescent yellow pigment. A numeral 9 indicates the yellow light reflected by the thermochromic layer 7.

EXAMPLE 7

The metallic luster pigment layer 3 was same as that in the example 1, while the thermochromic layer 7 of a thickness of about 40 μm was composed of the thermochromic material employed in the example 2, a fluorescent pink pigment and acrylic ester resin, and was capable of reversible change between athermally color-developed state and a color-extinguished state with the color of the fluorescent pink pigment, wiht luminocities of 2.3 and 5.5 respectively in the color-developed state and in the color-distinguished state.

At 15° C. or lower, there was exhibited silver luster color, which was replaced by the color of the fluorescent pink pigment at 30° C. or higher. A numeral 9 indicates the pink light reflected by the thermochromic layer 7.

EXAMPLE 8

The metallic luster pigment layer 3 was same as that in the example 1, while the thermochromic layer 7 of a thickness of about 40 μm was composed of the thermochromic material employed in the example 1, a fluorescent pink pigment, a blue pigment and acrylic ester resin, and was capable of reversible change between a thermally color-developed state and a color-extinguished state with lavender color obtained by mixing of the fluorescent pink pigment and the blue pigment, with luminocities of 2.4 and 5.5 respectively in the color-developed state and in the color-extinguished state. At 15° C. or lower, there was exhibited silver luster color, which was replaced, at 30° C. or higher, by lavender color obtained by mixing of the fluorescent pink pigment and the blue pigment. A numeral 9 indicates the lavender light reflected by the thermochromic layer 7.

EXAMPLE 9

The metallic luster pigment layer 3 was same as that in the example 1, while the thermochromic layer 7 of a thickness of about 40 μm was composed of the thermochromic material employed in the example 1, a blue pigment, a white pigment and acrylic ester resin, and was capable of reversible change between a thermally color-developed state and a color-extinguished state with pastel blue color obtained by mixing of the blue and white pigments, with luminocities of 2.2 and 5.4 respectively in the color-developed state and in the color-extinguished state. Similarly, at 15° C. or lower there was exhibited silver luster color, which was replaced, at 30° C. or hgiher, by pastel blue color obtained by mixing of the blue and white pigments. A numeral 9 indicates the pastel blue light reflected by the thermochromic layer 7.

EXAMPLE 10

FIG. 3 shows another embodiment of the present invention, consisting of a three-layered thermochromic laminate member, comprising layers 2, 3 same as in the example 1 and a third colored layer 8 containing a non-thermochromic coloring material and positioned adjacent to the thermochromic layer 2. In this example, the colored layer 8 had a thickness of about 10 μm and was fluorescent orange color, composed of a fluorescent orange pigment and acrylic ester resin, with a luminocity of 6.3. At 15° C. or lower, the thermochromic layer developed color, whereby the light 5 of a spectral region of 550–600 nm in the incident light was reflected while the light 6 of other wavelengths was absorbed, thus exhibiting silver luster color. At 30° C. or higher, the color of the thermochromic layer was extinguished, whereby the silver luster color was replaced by the color of the underlying fluorescent orange pigment. A numeral 10 indicates the orange light reflected by the layer 8.

EXAMPLE 11

The example 10 was reproduced except that the fluorescent orange pigment in the colored layer 8 was replaced by a fluorescent red pigment with a luminocity of 4.7, and that the thermochromic layer was replaced by a layer of a thickness of about 40 μm composed of acrylic ester resin and a thermochromic material in the form of microcapsules of an average particle size of 8 μm, which were obtained by interfacial polymerization microencapsulation with epoxy resin and an amine hardening agent, enclosing a thermochromic composition consisting of 3 parts of 2-anilino-3-methyl-6-dibutylaminofluorane, 6 parts of bisphenol-A, 25 parts of myristyl alcohol and 25 parts of cetyl caprate and which showed luminocities of 2.2 and 9.0 respectively in the color-developed state and in the color-extinguished state. At 20° C. or lower, the thermochromic layer developed color, whereby the light 5 consisting a part of the incident light was reflected while the light 6 of other wavelength was absorbed, thereby exhibiting silver luster color. At 20° C. or higher, the color of the thermochromic layer was extinguished, whereby the silver luster color was replaced by the color of the underlying fluorescent red pigment. A numeral 10 indicates the red light reflected by the layer 8.

EXAMPLE 12

The example 10 was reproduced except that the fluorescent orange pigment in the colored layer 8 was replaced by a fluorescent pink pigment with a luminocity of 5.6. At 20° C. or lower, the thermochromic layer similarly developed color, whereby the light 5 constituting a part of the incident visible light was reflected while the light 6 of other wavelengths was absorbed, thus silver luster color being exhibited. At 20° C. or higher, the color of the thermochromic layer was extinguished, whereby the silver luster color was replaced by the color of the underlying fluorescent pink pigment. A numeral 10 indicates the pink light reflected by the layer 8.

EXAMPLE 13

The example 10 was reproduced except that the fluorescent orange pigment in the colored layer 8 was replaced by a fluorescent green pigment with a luminocity of 8.2. At 20° C. or lower, the thermochromic layer similarly developed color, whereby the light 5 constituting a part of the incident visible light was reflected while the light 6 of other wavelengths was absorbed, thus silver luster color being exhibited. Above 20° C., the color of the thermochromic layer was extinguished, whereby the silver luster color was replaced by the color of the underlying fluorescent green pigment. A numeral 10 indicates the green light reflected by the layer 8.

Reference example 1

The example 1 was reproduced except that the thermochromic material therein was replaced by a thermochromic material in the form of microcapsules with an average particle size of 8 μm, which were obtained by interfacial polymerization microencapsulation with epoxy resin and an amine hardening agent, enclosing a thermochromic composition consisting of 6 parts of 2-anilino-3-methyl-6-dibutylaminofluorane, 10 parts of bisphenol-A and 25 parts of neopentyl stearate and not becoming colorless in the color-extinguished state, and which had luminocities of 4.5 and 6.0 respectively in the color-developed state and in the color-extinguished state. The thermochromic layer developed color at 15° C. or lower, whereby the light 5 constituting a part of the incident visible light was reflected while the light 6 of other wavelengths was absorbed, thus silver luster color being exhibited. However, in this reference example, since the thermochromic layer could sufficiently absorb the transmitted light in the color-extinguished state at 30° C. or higher, the exhibited color merely showed a slight loss of silver luster and still retained the silver luster.

Reference example 2

The metallic luster pigment layer 3 was same as that in the example 1, and the thermochromic layer 7 of a thickness of about 40 μm was composed of the thermochromic material employed in the example 1, a blue pigment and acrylic ester resin. The thermochromic layer developed color similar at 15° C. or lower whereby the light 5 constituting a part of the incident visible light while the light 6 of other wavelength was absorbed, thus silver luster color being exhibited. In this reference example, however, since the thermochromic layer was capable of sufficiently absorbing the transmitted light 6 even in the color-extinguished state at 30° C. or higher, the exhibited color merely changed to bluish silver and still retained silver luster.

Reference example 3

The example 10 was reproduced except that the fluorescent orange pigment therein was replaced by a colored layer 8 with a red pigment with a luminocity of 3.7. The thermochromic layer developer color similarly at 15° C. or lower, whereby the light 5 constituting a part of the incident visible light while the light 6 of other wavelengths was absorbed, thus silver luster color being exhibited. In this reference example, however, since the thermochromic layer was capable of sufficiently absorbing the transmitted light 6 even in the color-extinguished state at 30° C. or higher, the exhibited color merely changed to reddish silver and still retained silver luster.

In the following there will be explained examples of color change from metallic luster color, with reference to the attached drawings.

EXAMPLE 1

FIG. 1 illustrates the example 1, consisting of a two-layered thermochromic laminate member 1. A first layer 3 of a thickness of about 40 μm was composed of acrylic ester resin and a metallic luster red pigment consisting of natural mica particles surfacially coated with titanium oxide of 47 wt. % with an optical thickness of 265 nm and having a particle size of 10–60 μm, and said layer serves to regulate the wavelength of the reflected light.

There are also shown an incident light 4 and a reflected light 5. The non-reflected portion 6 of the incident light 4 is absorbed by a thermochromic layer 2.

A second thermochromic layer 2 of a thickness of about 40 μm was composed of a thermochromic material and acrylic ester resin. Said thermochromic material A consisted of microcapsules of an average particle size of 8 μm, formed by interfacial polymerization microencapsulation employing epoxy resin and an amine hardening agent, and enclosing solution of 3 parts of 2-anilino-3-methyl-6-dibutylaminofluorane, 6 parts of bisphenol-A and 50 parts of neopentyl stearate, and had luminocities of 2.2 and 9.0 respectively in the color-developed state and in the color-extinguished state, which were reversibly assumed by temperature change.

The thermochromic layer developed color at 15° C. or lower whereby the light 5 of a spectral region of 650–700 nm in the incident light was reflected while the light 6 of other wavelength was absorbed, thus metallic luster red color being exhibited. The thermochromic layer lost color at 30° C. or higher to reflect the transmitted light 6, whereby all the incident light was thus reflected and the metallic luster red color changed to colorless state.

EXAMPLE 2

The example 1 was reproduced except that the metallic luster red pigment therein was replaced by a metallic luster purple pigment consisting of natural mica particles surfacially coated with titanium oxide of 48 wt. % with an optical thickness of 295 nm and having a particle size of 10–60 μm.

The thermochromic layer developed color at 15° C. or lower whereby the light 5 in a spectral region of 380–430 nm in the incident light was reflected while the light 6 of other wavelengths was absorbed, thus metallic luster purple color being exhibited. The thermochromic layer lost color at 30° C. or higher to reflect the transmitted light 6, whereby all the incident light was reflected and the metallic luster purple color changed to colorless state.

EXAMPLE 3

The example 1 was reproduced except that the metallic luster red pigment therein was replaced by a metallic luster blue pigment consisting of natural mica particles surfacially coated with titanium oxide of 52 wt. % with an optical thickness of 330 nm and having a particle size of 10–60 μm.

The thermochromic layer developed color at 15° C. or lower whereby the light 5 in a spectral region of 430–500 nm in the incident light was reflected while the light 6 of other wavelengths was absorbed, thus metallic blue color being exhibited. The thermochromic layer lost color at 30° C. or higher to reflect the transmitted light 6, whereby all the incident light was reflected and the metallic blue color changed to colorless state.

EXAMPLE 4

The example 1 was reproduced except that the metallic luster red pigment therein was replaced by a metallic luster green pigment consisting of natural mica particles surfacially coated with titanium oxide of 57 wt. % with an optical thickness of 395 nm and having a particle size of 10–60 μm.

The thermochromic layer developed color at 15° C. or lower whereby the light 5 in a spectral region of 500–540 nm in the incident light was reflected while the light 6 of other wavelengths was absorbed, thus metallic luster green color being exhibited. The thermochromic layer lost color at 30° C. or higher to reflect the transmitted light 6, whereby all the incident light was reflected and the metallic luster green color changed to colorless state.

EXAMPLE 5

The example 1 was reproduced except the use of a thermochromic material which was similarly prepared by replacing 2-anilino-3-methyl-6-dibutylaminofluorane with 1.5 parts of 6-diethylaminobenzo(a)-fluorane and which showed luminocities of 4.2 and 8.8 respectively in the color-developed state and in the color-extinguished stae. At 15° C. or lower there was exhibited metallic magenta color, which changed to colorless state at 30° C. or higher.

EXAMPLE 6

The example 2 was reproduce except the use of a thermochromic material C which was similarly prepared by replacing 2-animino-3-methyl-6-dibutylaminofluorane therein with 1.5 parts of 6-diethylaminobenzo(a)-fluorane and 0.5 parts of 3-(4-diethylamino-2-ethoxyphenyl)-3-(1-ethyl-2-methylindol-3-yl)-4-azaphthalide and which showed luminocities of 3.8 and 8.7 respectively in the color-developed state and in the color-extinguished state. At 15° C. or lower there was exhibited metallic purple color, which changed to colorless state at 30° C. or higher.

EXAMPLE 7

The example 3 was reproduced except the use of a thermochromic material which was similarly prepared replacing 2-anilino-3-methyl-6-dibutylaminofluorane therein with 0.5 parts of 3-(4-diethylamino-2-ethoxyphenyl) -3-(1-ethyl-2-methylindol-3-yl)-4-azaphthalide and which showed luminocities of 3.4 and 8.8 respectively in the color-developed state and in the color-extinguished state. At 15° C. or lower there was similarly exhibited metallic blue color, which changed to colorless state at 30° C. or higher.

EXAMPLE 8

The example 4 was reproduced except the use of a thermochromic material which was similarly prepared by replacing 2-anilino-3-methyl-6-dibutylaminofluorane with 0.5 parts of 3,3-di(4-diethylamino-2-ethoxyphenyl)-4-azaphthalide and which showed luminocities of 5.1 and 8.9 respectively in the color-developed state and in the color-extinguished state. Similarly, at 15° C. or lower there was exhibited metallic green color, which changed to colorless state at 30° C. or higher.

EXAMPLE 9

FIG. 2 shows another embodiment of the present invention, wherein a first layer 3 was same as that in the example 1. A thermochromic layer 7 of a thickness of about 40 μm was composed of a thermochromic material, a blue pigment, a white pigment and acrylic ester resin, and was capable of reversible change between a thermally color-developed state and pastel blue color obtained by mixing of the blue and white pigments, with luminocities of the mixture of 2.5 and 8.9 respectively in the color-developed state and in the color-extinguished state.

The thermochromic layer developed color at 15° C. or lower whereby the light 6 of a spectral region of 650–700 nm in the incident light was reflected while the light 6 of other wavelengths was absorbed, thus metallic luster red color being exhibited. The color of the thermochromic layer was extinguished at 30° C. or higher, whereby the metallic luster red color was replaced by pastel blue color obtained by mixing of the blue and white pigments. A numeral 9 indicates the pastel blue light reflected by the thermochromic layer 7.

EXAMPLE 10

The metallic luster pigment layer 3 was same as that in the example 9, while the thermochromic layer 7 of a thickness of about 40 μm was composed of the thermochromic material employed in the sample 5, a fluorescent orange pigment and acrylic ester resin, and was capable of reversible change between a thermally color-developed state and a color-extinguished state with the color of the fluorescent orange pigment, with luminocities of the mixture of 2.5 and 8.9 respectively in the color-developed state and in the color-extinguished state. Similarly, at 15° C. or lower there was exhibited metallic luster red color, which was replaced, at 30° C. or higher, by the color of the fluorescent orange pigment. A numeral 9 indicates the orange light reflected by the layer 7.

EXAMPLE 11

The metallic luster pigment layer 3 of a thickness of about 40 μm was composed of a metallic luster red pigment, consisting of natural mica particles surfacially coated with titanium oxide of 45 wt. % and further with ion oxide of 4 wt. % with a combined optical thickness of 270 nm and having a particle size of 10–50 μm, and acrylic ester resin. The thermochromic layer 7 of a thickness of about 40 μm was composed of the thermochromic material employed in the example 1, a fluorescent yellow pigment and acrylic ester resin, and was capable of reversible change between a thermally color-developed state and the color of the fluorescent yellow pigment, with luminocities of the mixture of 2.2 and 8.9 respectively in the color developed state and in the color-extinguished state.

The thermochromic layer developed color at 15° C. or lower whereby the light 5 of a spectral region of 650–700 nm in the incident light was reflected, while the light 6 of other wavelengths was absorbed, thus metallic luster reddish purple color being exhibited. The color of the thermochromic layer was extinguished at 30° C. or higher, whereby said metallic luster reddish purple color was replaced by the color of the fluorescent yellow pigment. A numeral 9 indicates the yellow light reflected by the thermochromic layer 7.

EXAMPLE 12

The metallic luster pigment layer 3 was same as that in the example 2, while the thermochromic layer 7 of a thickness of about 40 μm was composed of the thermochromic material employed in the example 1, a fluorescent green pigment and acrylic ester resin, and was capable of reversible change between a thermally color-developed state and a color-extinguished state with the color of the fluorescent green pigment, with luminocities of the mixture of 2.3 and 8.0 respectively in the color-developed and in the color-extinguished state.

The thermochromic layer developed color at 15° C. or lower whereby the light 5 of a spectral region of 380–430 nm in the incident light was reflected while the light 6 of other wavelengths was absorbed, thus metallic luster purple color being exhibited. The color of the thermochromic layer was extinguished at 30° C. or higher, whereby the metallic luster purple color was replaced by the color of the fluorescent green pigment. A numeral 9 indicates the green light reflected by the thermochromic layer 7.

EXAMPLE 13

The metallic luster pigment layer 3 was same as that in the example 3, while the thermochromic layer 7 of a thickness of about 40 μm was composed of the thermochromic material employed in the example 1, a fluorescent red pigment and acrylic ester resin, and was capable of reversible change between a thermally color-developed state and a color-extinguished state with the color of the fluorescent red pigment, with luminocities of the mixture of 2.4 and 4.8 respectively in the color-developed state and in the color-extinguished state.

The thermochromic layer developed color at 15° C. or lower whereby the light 5 of a spectral region of 430–500 nm in the incident light was reflected while the light 6 of other wavelengths was absorbed, thus metallic luster blue color being exhibited. The color of the thermochromic layer was extinguished at 30° C. or higher, whereby the metallic luster blue color was replaced by the color of the fluorescent red pigment. A numeral 9 indicates the red light reflected by the thermochromic layer 7.

EXAMPLE 14

The metallic luster pigment layer 3 was same as that in the example 4, while the thermochromic layer 7 of a thickness of about 40 μm was composed of the thermochromic material employed in the example 1, a fluorescent pink pigment, a blue pigment and acrylic ester resin, and was capable of reversible change between a thermally color-developed state and a color-extinguished state with lavender color obtained by the mixing of the fluorescent pink pigment and the blue pigment, with luminocities of the mixture of 2.3 and 5.5 respectively in the color-developed state and in the color-extinguished state. The thermochromic layer developed color at 15° C. or lower whereby the light 5 of a spectral region of 500–540 nm in the incident light was reflected while the light 6 of other wavelengths was absorbed, thus metallic luster green color being exhibited. The color of the thermochromic layer was extinguished at 30° C. or higher, whereby the metallic luster green color was replaced by lavender color obtained by mixing of the fluorescent pink pigment and the blue pigment. A numeral 9 indicates the lavender light reflected by the thermochromic layer 7.

EXAMPLE 15

FIG. 3 shows another embodiment of the present invention, consisting of a three-layered thermochromic laminate member, comprising layers 2, 3 same as in the example 5 and a third colored layer 8 containing a non-thermochromic color material and positioned adjacent to the thermochromic layer 2. In this example, the colored layer 8 had a thickness of about 10 μm and was fluorescent yellow color, composed of a fluorescent yellow pigment and acrylic ester resin, with a luminocity of 8.9. The thermochromic layer developed color at 15° C. or lower whereby the light 5 of a spectral region of 650–700 nm in the incident light was reflected while the light 6 of other wavelengths was absorbed, thus metallic luster red color being exhibited. The color of the thermochromic layer was extinguished at 30° C. or higher, whereby the metallic luster red color was replaced by the color of the underlying fluorescent yellow pigment. A numeral 10 indicates the yellow light reflected by the non-thermochromic colored layer 8.

EXAMPLE 16

The metallic luster pigment layer 3 was same as that in the example 2, while the thermochromic layer 2 of a thickness of about 40 μm was composed of a thermochromic material and acrylic ester resin. Said thermochromic materail had the form of microcapsules of a particle size of 8 μm, which were obtained by interfacial polymerization microencapsulation employing epoxy resin and an amine hardening agent and enclosing a thermochromic composition consisting of 3 parts of 2-anilino-3-methyl-6-dibutylaminofluorane, 6 parts of bisphenol-A, 25 parts of myristyl alcohol and 25 parts of cetyl caprate and which showed luminocities of 2.2 and 9.0 respectively in the color-developed state and in the color-extinguished state. The colored layer 8 of a thickness of about 10 μm was of fluorescent orange color and was composed of a fluorescent orange pigment and acrylic ester resin, with a luminocity of 6.3.

The thermochromic layer developed color at 20° C. or lower whereby the light 5 of a spectral region of 380–430 nm in the incident light was reflected while the light 6 of other wavelength was absorbed, thus metallic luster purple color being exhibited. The color of the thermochromic layer was extinguished at 20° C. or higher, whereby the metallic luster purple color was replaced by the color of the underlying fluorescent orange pigment. A numeral 10 indicates the orange light reflected by the non-thermochromic layer 8.

EXAMPLE 17

The example 16 was reproduced except the thermochromic material therein was replaced by a thermochromic material in the form of microcapsules enclosing the thermochromic material of the example 5. Similarly the thermochromic layer developed color at 15° C. or lower whereby the light 5 of a spectral region of 380–430 nm in the incident light was reflected while the light 6 of other wavelengths was absorbed, thus metallic luster magneta color being exhibited. The color of the thermochromic layer was extinguished at 30° C. or higher, whereby the metallic luster magenta color was replaced by the color of the underlying fluorescent orange pigment. A numeral 10 indicates the orange light reflected by the non-thermochromic colored layer 8.

EXAMPLE 18

The example 16 was reproduced except that the metallic luster pigment therein was replaced by that employed in the example 3 and the fluorescent orange pigment in the colored layer 8 was replaced by a fluorescent pink pigment with a luminocity of 5.5. Similarly the thermochromic layer developed color below 20° C. whereby the light 5 of a spectral region of 430–500 nm in the incident light was reflected while the light 6 of other wavelengths was absorbed, thus metallic luster blue color being exhibited. The color of the thermochromic layer was extinguished above 20° C., whereby the metallic luster blue color was replaced by the color of the underlying fluorescent pink pigment. A numeral 10 indicates the pink light reflected by the non-thermochromic colored layer 8.

EXAMPLE 19

The example 18 was reproduced except that the fluorescent pigment in the colored layer 8 therein was replaced by a fluorescent yellow pigment with a luminocity of 8.4. Similarly the thermochromic layer developed color below 20° C. whereby the light 5 of a spectral region of 430–500 nm in the incident light was reflected while the light 6 of other wavelengths was absorbed, thus metallic luster blue color being exhibited. The color of the thermochromic layer was extinguished above 20° C., whereby the metallic luster blue color was replaced by the color of the underlying fluorescent yellow pigment. A numeral 10 indicates the yellow light reflected by the non-thermochromic colored layer 8.

EXAMPLE 20

The example 16 was reproduced except that the metallic luster pigment therein was replaced by that employed in the example 4 and that the fluorescent orange pigment in the colored layer 8 was replaced by a fluorescent red pigment with a luminocity of 4.7. Similarly the thermochromic layer developed color below 20° C. whereby the light 5 of a spectral region of 500–540 nm in the incident light was reflected while the light 6 of other wavelengths was absorbed, thus metallic luster green color being exhibited. The color of the thermochromic layer was extinguished above 20° C., whereby the metallic luster green color was replaced by the color of the underlying fluorescent red pigment. A numeral 10 indicates the red light reflected by the non-thermochromic colored layer 8.

EXAMPLE 21

The example 20 was reproduced except that the fluorescent red pigment in the colored layer 8 therein was replaced by a blue pigment and a white pigment, with a luminocity of 5.0. Similarly the thermochromic layer developed color below 20° C., whereby the lgiht 5 of a spectral region of 500–540 nm in the incident light was reflected while the light 6 of other wavelengths was absorbed, thus metallic luster green color being exhibited. The color of the thermochromic layer was extinguished above 20° C., whereby the metallic luster green color was replaced by pastel blue color obtained by the mixing of the underlying blue and white pigments. A numeral 10 indicates the pastel blue light reflected by the non-thermochromic colored layer 8.

Reference example 1

The example 1 was reproduced except that the thermochromic material therein was replaced by a thermochromic material in the form of microcapsules with an average particle size of 8 μm, which were obtained by interfacial polymerization microencapsulation with epoxy resin and an amine hardening agent, enclosing a thermochromic composition consisting of 6 parts of 2-anilino-3-methyl-6-dibutylaminofluorane, 10 parts of bisphenol-A, and 25 parts of neopentyl stearate and not becoming colorless in the color-extinguished state, and which has luminocities of 4.5 and 6.0 respectively in the color-developed state and in the color-extinguished state. The thermochromic layer developed color at 15° C. or lower, thereby the light 5 of a spectral region of 490–500 nm in the incident light was reflected while the light 6 of other wavelengths was absorbed, thus metalling luster blue color being exhibited. In this reference example, however, since the thermochromic layer was capable of sufficiently absorbing the transmitted light 6 even in the color-extinguished state at 30° C. or above, the metallic luster blue color became somewhat thinner but was still perceivable, and reversible change between the metallic blue color and the colorless state could not be attained.

Reference example 2

The metallic luster pigment layer 3 was same as that in the example 9, while the thermochromic layer 7 of a thickness of about 40 μm was composed of the thermochromic material employed in the reference example 1, a blue pigment and acrylic ester resin, with luminocities of 2.5 and 3.3 respectively in the color-developed state and in the color-extinguished state. The thermochromic layer developed color similarly at 15° C. or lower whereby the light 5 of a spectral region of 650–700 nm in the incident light was reflected while the light 6 of other wavelengths was absorbed, thus metallic luster red color being exhibited. In this reference example, however, since the thermochromic layer was capable of sufficinetly absorbing the transmitted light 6 even in the color-extinguished state at 30° C. or higher, the exhibited color merely changed to somewhat bluish metallic red color but still retained metallic luster red color, and the reversible change between the metallic red color and the colorless state could not be attained.

Reference example 3

The example 16 was reproduced except that the fluorescent orange pigment therein was replaced by a red pigment layer as the colored layer 8, with a lumiocity of 3.7. The thermochromic layer similarly developed color below 20° C., whereby the light 5 of a spectral region of 380–430 nm in the incident light was reflected while the light 6 of other wavelengths was absorbed, thus metallic luster purple color being exhibited. In this reference example, however, since the thermochromic layer was capable of sufficiently absorbing the transmitted light 6 even in the color-extinguished state above 20° C., the exhibited color merely changed to somewhat reddish metallic purple color and still retained metallic purple luster, and the reversible change between the metallic purple color and the red color could not be attained.

In the following there will be explained examples of application of the thermochromic laminate member of the present invention, and at first shown are applications to toys.

Application example 1

Preparation of a doll dress (gold—rainbow color)

On a synthetic leather sheet consisting of polyvinyl chloride resin, stripe patterns were printed with commercial screen printing inks (non-thermochromic) of yellow, green, pink, orange and blue. Then a thermochromic layer 2 of a thickness of 40 μm was formed on the entire surface, bearing said stripe patterns thereon, by printing with a 100-mesh screen, employing thermochromic screen printing ink consisting of dispersion of a thermochromic color-memorizing pigment (black-colorless; color-extinguishing temperature 30° C., color-developing temperature 15° C.).

Then, on said thermochromic layer 2, there was formed a metallic luster pigment layer 3 of a thickness of 40 μm, by printing through a 100-mesh screen with screen printing ink containing gold luster pigment.

The obtained sheet, which appeared gold color, showed the stripe pattern of the above-mentioned five colors when locally heated to 30° C. or higher, and retained said stripe pattern at room temperature.

Said heated area returned to gold color when it was cooled to 15° C. or lower, and the entire sheet appeared gold color.

Also after being converted into the stripe-patterned state by heating entirely to 30° C. or higher, said sheet showed gold color when locally cooled to 15° C. or lower, and retained the gold color pattern at the room temperature. When subsequently heated to 30° C. or higher, the gold color disappeared and the entire sheet returned to the stripe-patterned state.

Costumes (jacket and skirt) of a doll were prepared by cutting and sewing said sheet. Said costumes could arbitrarily show gold color or colorful strip patterns at the room temperature, and the user could exhibit various modes by locally generating gold color or stripe patterns.

| [Composition of thermochromic color-memorizing screen printing ink] | |
| --- | --- |
| 15 parts | thermochromic color-memorizing pigment |
| 40 parts | vinyl acetate-vinyl chloride copolymer resin |
| 0.5 parts | silicone defoamer |
| 20 parts | xylene |
| 10 parts | methylisobutylketone |
| 15 parts | aromatic medium-boiling solvent |
| [Composition of screen printing ink containing metallic luster pigment] | |
| 14 parts | metallic luster gold pigment (Iriodine 205) |
| 40 parts | vinyl acetate-vinyl chloride copolymer |
| 0.5 parts | silicone defoamer |
| 10 parts | xylene |
| 20 parts | methyl isobutylketone |
| 15 parts | aromatic medium-boiling solvent. |

Iriodin is the trande name of the metallic luster gold pigment manufactured by Merck Japan, and #205 indicates the product number (hereinafter likewise indicated).

The parts in the composition indicate the parts by weight, In the following compositions the quantities are likewise indicated, Application example 2

On a white satin cloth, a thermochromic layer 7 (thickness 35 μm) in the heart-shaped patterns was formed by printing, through a 100-mesh screen, of thermochromic screen printing inks of five colors (black—fluorescent pink, black—fluorescent yellow, black—fluorescent green, black fluorescent red, and black—fluorescent blue) having a color-varying temperature of 30° C.

Then, on thus prepared thermochromic layer 7 of heart-shaped patterns, a metallic luster pigment layer 3 of a thickness of 40 μm by overlay printing of the heart-shaped patterns with screen printing ink containing a silver luster pigment. An acrylic top coating of a thickness of about 20 μm was further formed thereon.

A casual dress for a doll was prepared by cutting and sewing thus formed cloth. Said dress showed silver-colored heart-shaped patterns on white background, but, when breath is blown to heart-shaped patterns, said patterns changed to pearl pink, pearl yellow, pearl green, pearl red and pearl blue. Thus varied colors returned to the silver color at the room temperature, and the color variation between the silver color and the various colors could be repeated.

| [Composition of thermochromic screen printing ink] | |
|---|---|
| 10 parts | thermochromic color-memorizing pigment |
| 0.2–2 parts | ordinary pigment (pink, yellow, green, red or blue) |
| 10 parts | acrylic ester emulsion |
| 10 parts | mineral terpene emulsion |
| 0.2 parts | crosslinking agent |
| 0.01 parts | defoamer |
| [Composition of screen printing ink containing metallic luster pigment] | |
| 10 parts | silver luster pigment (Iriodin 100; Merck Japan) |
| 40 parts | acrylic ester resin |
| 0.5 parts | silicone defoamer |
| 20 parts | butyl acetate |
| 10 parts | xylene |
| 10 parts | aromatic medium-boiling solvent |

Application example 3

A metalllic luster thermochromic toy 1 was prepared by forming, in the following parts of a doll made of polyvinyl chloride resin, a thermochromic layer 7 by spraying a thermochromic spray paint, then forming a metallic luster pigment layer 3 by spraying a spray paint containing a metallic luster pigment, and finally spraying a clear coating.

The sprayed portions, thermochromic layers 7, metallic luster pigments layer 3 and the obtained color changes as follows:

Lips [thermochromic layer: black—pink (color developed at 15° C., color extinguished at 30° C.); metallic luster pigment layer: Iriodin 205; color change; gold—pearl pink (changes at 15° C. and 30° C.)], Eye shadows [thermochromic layer: black—lavender (color developed at 15° C., color extinguished at 30° C.); metallic luster pigment layer: Iriodin 100; color change; silver—pearl lavender (changes at 15° C. and 30° C.)], Earrings [thermochromic layer: black—orange (color developed at 15° C., color extinguished at 30° C.); metallic luster pigment layer: Iriodin 225; color change: metallic blue—pearl orange (changes at 15° C. and 30° C.)], and Manicure [thermochromic layer: black—pink (color developed at 15° C., color extinguished at 30° C.); metallic luster pigment layer: Iriodin 235; color change: metallic green—pearl pink (changes at 15° C. and 30° C.)].

Thus obtained doll, at the room temperature after being heated to 30° C. or higher, showed a state of ordinary light make-up, with pink lips, lavender eye shadows, orange earrings and pink nails. When these areas were cooled with a make-up utensil filled with iced water, the doll varied to a sychedelic make-up with gold lip, silver eye shadows, metallic blue earrings and metallic green manicure, and this state was stably maintained at the room temperature. The original ordinary make-up was restored by heating said areas with a make-up utensil filled with warm water or a cloth impregnated with warm water.

| [Composition of thermochromic color-memorizing spray paint] | |
|---|---|
| 10 parts | thermochromic pigment (black - colorless (color developed at 15° C. and extinguished at 30° C.) |
| 0.2–2 parts | ordinary pigment (pink, lavender or orange) |
| 45 parts | 50% solution of acrylic resin in xylene |
| 20 parts | xylene |
| 20 parts | methylisobutylketone |
| [Composition of spray paint containing metallic luster pigment] | |
| 2 parts | metallic luster pigment |
| 45 parts | 50% xylene solution of acrylic resin |
| 20 parts | xylene |
| 20 parts | methylisobutylketone |

Application example 4

A zinc die-cast miniature car was painted white by electrostatic painting at 90,000 V, employing an automatic disk-type electrostatic painting machine and utilizing a white alkyd-melamine spray paint for electrostatic painting, and a thermochromic color-memorizing spray paint for electrostatic painting was similarly painted with the automatic disk-type electrostatic painting machine at 90,000 V.

After hardening for 15 minutes at 100° C., a spray paint for electrostatic painting containing a metallic luster pigment was similarly applied, and was hardened for 15 minutes at 100° C. Finally a clear coat for electrostatic painting was similarly applied and hardened for 15 minutes at 100° C. to obtain a thermochromic miniature car of metallic luster, with color-memorizing character.

The obtained miniature car changed to silver color when cooled to 15° C. or lower, and retained the silver color at the room temperature. It changed to pearl blue color when heated to 35° C. or higher, and remained in this state at the room temperature. Also when the roof portion was cooled to 15° C. or lower, said portion alone changed to silver color, and the obtained two-tone color state remained at the room temperature.

| [Composition of thermochromic color-memorizing spray paint for electrostatic painting] | |
|---|---|
| 15 parts | thermochromic pigment (black - colorless; color developed at 15° C. and extinguished at 30° C.) |
| 0.5 parts | ordinary blue pigment |
| 35 parts | 50% xylene solution of alkyd resin |
| 0.5 parts | additive |
| 30 parts | xylene |
| 20 parts | butyl acetae |
| 10 parts | butyl cellosolve |
| 6 parts | melamine resin |
| [Composition of metallic luster pigment-containing spray paint for electrostatic painting] | |
| 4 parts | silver luster pigment (Superwhite (trade name), Mearl corporation (U.S.A.)) |
| 35 parts | 50% xylene solution of alkyd resin |
| 0.5 parts | additive |
| 30 parts | xylene |
| 20 parts | butyl acetate |
| 10 parts | butyl cellosolve |
| 6 parts | melamine resin |

Application example 5

On a white doll crown made of styrol resin, heat-shaped patterns were formed with a thermochromic color-memorizing spray paint (black—green, color developed at 20° C. and extinguished at 30° C.), and the remaining area was sprayed with another thermochroic color-memorizing spray ink (black—pink, color developed at 20° C. and extinguished at 30° C.). Then the entire surface of the crown was sprayed with a spray paint containing a gold luster pigment and finally with a lustrous clear coating.

Thus prepared crown, which was gold at 20° C. or lower, changed to pink color with green heart-shaped patterns when heated to 30° C. or higher and retains this state at the room temperature. It returns to the gold color when cooled to 20° C. or lower and retained this state at the room temperature.

| [Composition of thermochromic color-memorizing spray paint] | |
|---|---|
| 15 parts | thermochromic color-memorizing pigment (black - colorless, color developed at 20° C. and extinguished at 30° C.) |
| 3 parts | ordinary fluorescent pink pigment |
| 40 parts | 50% xylene solution of acryl polyol |
| 6 parts | polyisocyanate hardening agent |
| 40 parts | xylene |
| [Composition of thermochromic color-memorizing spray paint] | |
| 15 parts | thermochromic color-memorizing pigment (black - colorless, color developed at 20° C. and extinguished at 30° C.) |
| 1 part | ordinary green pigment |
| 40 parts | 50% xylene solution of acrylopolyol |
| 6 parts | isocyanate hardening agent |
| 40 parts | xylene |
| [Composition of metallic luster pigment-containing spray paint] | |
| 3 parts | gold luster pigment (Iriodin 205) |
| 40 parts | 50% xylene solution of acrylopolyol |
| 6 parts | polyisocyanate hardening agent |
| 40 parts | xylene |
| [Composition of lustrous clear coat] | |
| 40 parts | 50% xylene solution of acrylopolyol |
| 6 parts | polyisocyanate hardening agent |
| 40 parts | xylene |

Application example 6

A toy robot was injected molded, at a cylinder temperature of 180° C. and a nozzle temperature of 170° C., utilizing a mixture of 20 parts of a thermochromic pigment (black—colorless), 1.5 parts of an ordinary yellow pigment and 1000 parts of polystyrene. On said toy robot, following three spray paints containing metallic luster pigments were spray coated, and a clear top coating was sprayed over the entire surface.

| [Compositions of metallic luster pigment-containing spray paints] | |
|---|---|
| Body: | 3 parts of Iriodin 100 in a vehicle cosisting of 40 parts of 50% xylene solution of acrylic resin; |
| Head: | 3 parts of Iriodin 205 in said vehicle; and |
| Legs: | 3 parts of Iriodin 219 in said vehicle. |

Thus obtained toy robot was yellow at the room temperature (ca. 25° C.), but changed, when immersed in iced water, to gold color in the head, metallic purple in the legs and silver color in other parts. When left at the room temperature (ca. 25° C.), the toy robot returned to yellow color in the entire parts.

Application example 7

A doll pendant made of pale orange ABS resin was manually sprayed with a thermochromic color-memorizing spray paint (consisting of 40 parts of a thermochromic color-memorizing pigment (brown—black, color developed at 18° C. and extinguished at 32° C.), 2 parts of an ordinary fluorescent pink pigment, 1 part of a fluorescent orange pigment, 40 parts of 50% xylene solution of acrylic resin, and 40 parts of xylene). Then it was sprayed with a gold luster pigment-containing spray paint (consisting of 3 parts of Hi-Lite Colors Gold (trade name of The Mearl Corporation (U.S.A.), 40 parts of 50% xylene solution of acrylic resin and 40 parts of xylene) to obtain a thermochromic pendant.

When cooled to 18° C. or lower, said pendant changed to reddish gold color and retained said color at the room temperature. When heated to 32° C. or higher, it changed to red color which was retained at the room temperature. Upon cooled to 18° C. or lower again, it changed to gold color which was retained at the room temperature.

In the following there will be explained applications to accessories.

Application example 1

A barrette, formed by connecting four white heart-shaped articles molded from styrol resin, was colored in the following manner.

On the first molded article, there were laminated a color-memorizing thermochromic layer 7A (black—pink, color changes at 15° C. and 32° C.), then a gold luster pigment layer 3A, containing Iriodin 205, and finally a lustrous top coating 5. Similarly, on the second molded article, there were formed a color-memorizing thermochromic layer 7B (black—green, color changes at 15° C. and 32° C.), and a silver luster pigment layer 3B containing Iriodin 100. On the third molded article there were fomed a color-memorizing therochromic layer 7C (black—yellow, color changes at 15° C. and 32° C.) and a gold luster pigment layer 3C. On the fourth molded article there were formed a color-memorizing thermochromic layer 7D (black—blue, color changes at 15° C. and 32° C.) and a silver luster pigment 3D. Finally a clear coating was applied onto these molded articles. Iriodin is the trade name of Merck Japan, and the following number indicates the product grade.

The above-mentioned thermochromic layers 7A-7D were prepared with spray paints of the following compositions A-D.

The spray paint A consisted of 15 parts of a thermochromic color-memorizing pigment (black—colorless, color changes at 15° C. and 32° C.) and 3 parts of an ordinary fluorescent pink pigment, dispersed in 40 parts of 50% xylene solution of acrylic resin. The spray paint B consisted of 0.05 parts of an ordinary blue pigment and 0.5 parts of an ordinary yellow pigment instead of the ordinary pigment in the composition A. The spray paint C consisted of 1 part of an ordinary yellow pigment instead of the ordinary pigment in said composition A. The spray paint D consisted of 0.3 parts of an ordinary blue pigment instead of the ordinary pigment in said composition A. The metallic luster pigment layers 3A-3D were obtained by dispersing 3 parts of respective metallic luster pigments in a vehicle consisting of 40 parts of 50% xylene solution acrylic resin and 40 parts of xylene. Thus obtained thermochromic barrette, which was gold in the first and third molded articles and silver in the second and fourth molded articles at 15° C. or lower, changed to pink, green, yellow and blue in said first, second, third and fourth molded articles at 32° C. or higher, and retained this state at the room temperature. When cooled again to 15° C. or lower, the barrette returned to the original state with gold and silver colors, and retained this state at the room temperature. Thus this barrette can have two designs (color states), which can be arbitrarily selected by the user.

Application example 2

A necklace, consisting of plural metal stars, was sprayed with white acrylic paint, and, after drying, was colored in the following manner.

On a first star, there were formed a color-memorizing thermochromic layer 7E (black—pink, color changes at 15° C. and 38° C.), then a metallic luster purple pigment layer 3E, obtained from a paint prepared from 3 parts of Iriodin 219 dispersed in a vehicle consisting of 40 parts of 50% xylene solution of acrylpolyol, 6 parts of a polyisocyanate hardening agent and 40 parts of xylene, and finally a lustrous clear coating. Similarly color-memorizing thermochromic layers F, G, H, I (color change temperatures being same as those in the layer 7E) were formed respectively on a second star (black—yellow), a third star (black—blue), a fourth star (black—orange) and a fifth start (black—green). Subsequently a metallic luster pigment layer 3 was formed with the same paint as for the layer 3E, on each thermochromic layer 7, and the lustrous clear coating was applied.

Said thermochromic layers 7E-7I were prepared with the following spray paints E-I.

The spray paint E was obtained by dispersing 15 parts of a color-memorizing thermochromic pigment (color changes at 15° C. and 38° C.) and 3 parts of an ordinary fluorescent pink pigment in a vehicle consisting of 40 parts of 50% xylene solution of acrylic resin, 6 parts of a polyisocyanate hardening agent and 40 parts of xylene. The spray paints F, G, H, I were respectively obtained by replacing the ordinary pigment in the paint E with 1.5 parts of a yellow pigment, 0.2 parts of a blue pigment, 0.5 parts of an orange pigment, and 0.7 parts of a yellow pigment combined with 0.05 parts of a blue pigment. The first to fifth stars of thus prepared thermochromic necklace were all metallic purple at 15° C. or lower, but the second to fifth stars varied respectively to pink, yellow, blue and orange when heated to 38° C. or higher and retained this state at the room temperature. When cooled again to 15° C. or lower, all the stars returned to metallic purple and retained this state at the room temperature. Thus this necklace can provide two designs in reversible manner, which the user can arbitrarily select.

Application example 3

A ribbon-shaped broach was obtained by injection molding, at a cylinder temperature of 180° C. and a nozzle temperature of 175° C., of a mixture of 20 parts of a thermochromic pigment (black—colorless. color change at 12° C.), 4 parts of an ordinary fluorescent pink pigment and 1000 parts of high-impact polystyrene. Then sprayed thereon were a metallic luster pigment-containing spray paint, consisting of 3 parts of a silver luster pigment (Superwhite (trade name) supplied by The Mearl Corporation (U.S.A.)), 40 parts of 50% xylene solution of acrylic resin and 40 parts of methylisobutylketone, and finally a lustrous clear top coating.

Thus prepared thermochromic broach, which was pink at the room temperature, changed to silver color when cooled to 12° C. or lower. It returned to the original pink color when left at the room temperature above 12° C.

Application example 4

A picture of an automobile was printed with ordinary offset printing ink on synthetic paper. Then thermochromic screen printing ink (black—colorless, color change at 30° C.) was applied over the entire surface, covering said picture, and ink containing a metallic luster pigment was screen printed thereon over the entire surface. Subsequently the synthetic paper was cut in the size of said picture, applied to a flat part of a key holder and potted with ultraviolet-settable acrylic resin to obtain a thermochromic key holder.

| [Composition of thermochromic screen printing ink] | |
|---|---|
| 10 parts | thermochromic pigment (black - colorless, color change at 30° C.) |
| 10 parts | ethylene-vinyl acetate copolymer emulsion |
| 30 parts | 7% aqueous solution of carboxy cellulose |
| 0.05 parts | defoamer |
| [Composition of metallic luster pigment-containing screen printing ink] | |
| 3 parts | Iriodin 205 (Merck Japan) |
| 30 parts | 50% xylene solution of acrylic resin |
| 10 parts | vinyl chloride-vinyl acetate copolymer |
| 5 parts | xylene |
| 5 parts | methylbutylketone |
| 10 parts | aromatic medium-boiling solvent |
| 0.1 parts | deformer |

The key holder thus prepared was gold color, which was replaced by the picture of automobile when warmed with hand. It returned to gold color when left at the room temperature.

In the following there will be explained applications or artificial nails.

Application example 1

On an artificial nail made of acetyl cellulose resin, there were sprayed manually a thermochromic color-memorizing spray paint, consisting of 15 parts of a thermochromic color-memorizing pigment (black—colorless, color generated at 15° C. and extinguished at 38° C.), 3 parts of an ordinary fluorescent pink pigment, 40 parts of 50% xylene solution of acrylic resin, 10 parts of xylene and 30 parts of methylisobutylketone, and a gold luster pigment-containing spray paint, consisting of 3 parts of Hi-Lite Colors Gold (trade name) of The Mearl Corporation (U.S.A.), 40 parts of 50% xylene solution of acrylic resin, 10 parts of xylene and 30 parts of methylisobutylketone, thereby obtaining a thermochromic artificial nail.

Said thermochromic artificial nail, which was gold at 15° C. or lower, changed to pink color when warmed to 38° C. or higher and retained this state at the room temperature. When cooled to 15° C. or lower, it returned to gold color and retained this state at the room temperature. Thus this artificial nail has two colors, which the user can arbitrarily select. Since the color changing temperature at the higher temperature side is 38° C., the color change did not take place by body temperature or by ambient temperature, and the selected color could be stably maintained.

Application example 2

On an artificial nail made of pale yellow polyamide resin, heart-shaped marks of pink and black colors were printed with ordinary tampon printing inks. Then there were thereon sprayed, with a hand spray, a thermochromic color-memorizing spray paint consisting of a thermochromic color-memorizing pigment (black—colorless, color changes at 17° C. and 32° C.), 40 parts of 50% xylene solution of acrylpolyol, 6 parts of a polyisocyanate hardening agent and 40 parts of xylene, then a silver luster pigment-containing spray paint, consisting of 3 parts of Iriodin 200 (trade name) of Merck Japan, 40 parts of 50% xylene solution of acrylpolyol, 6 parts of a polyisocyanate hardening agent and 40 parts of xylene, and finally a lustrous clear top coating, thereby obtaining a thermochromic color-memorizing nail was silver color at 17° C. or lower, but, when heated to 32° C. or higher, the silver color was replaced by heart-shaped patterns of pearl pink and pearl blue on white background, and this state was retained at the room temperature. When cooled to 15° C. or lower, the nail returned to silver color and retained this state at the room temperature.

Application example 3

A thermochromic artificial nail 1 was formed by injection molding, at a cylinder temperature of 180° C. and a nozzle temperature of 175° C., of a mixture of 20 parts of a thermochromic pigment (black—colorless, color change at 18° C.), 4 parts of an ordinary fluorescent pink pigment and 1000 parts of high-impact polystyrene. Then there was sprayed a metallic luster spray paint consisting of 3 parts of a metallic luster blue pigment (Iriodin 225 (Merck Japan), 40 parts of 50% xylene solution of acrylic resin and 40 parts of methylisobutylketone, and finally a lustrous clear top coating was applied by spraying.

Thus prepared thermochromic artificial nail was pink colored in the normal state, and changed to metallic blue color when cooled to 18° C. or lower. It returned again to pink color at the room temperature, beyond 18° C.

Therefore, said artificial nail is pink colored when worn in the indoor, but changes to metallic blue color outdoors in the winter time.

As detailedly explained in the foregoing, the thermochromic laminate member of the present invention can exhibit color changes from gold or silver color, or from metallic luster colors such as metallic red, metallic purple, metallic blue or metallic green, thereby improving the variety, of colors, delicateness, unexpectedness and decorative character of color changes, and is applicable in various fields such as toys, decorations, printing etc.

The thermochromic laminate member of the present invention retains the thermochromic function of the conventional thermochromic material and enhances the concealing effect, utilizing the light reflecting effect of the metallic luster pigment layer, thereby concealing and exhibiting a colored layer of various colors and densities by a temperature change.

Said color change occurs in highly responsive manner in a system in which the thermochromic layer is formed with a thermochromic material of a small hysteresis, and with a reasonable response to temperature change if the thermochromic material of a medium hysteresis is employed. If the thermochromic material with a large hysteresis (including a color-memorizing thermochromic dye) is employed, a state varied by heat or coldness is retained after the removal of such heat or coldness and can be perceived at the room temperature.

What is claimed is:

1. A thermochromic laminate member capable of reversible change between a metallic luster color and a colorless state, comprising:

A) a first layer for regulating the wavelength of reflected light, composed of a metallic luster pigment, which consists of natural mica particles surfacially coated with titanium oxide and which has a particle size of 5 to 100 $\mu$m, and a film forming material; and B) a second layer composed of a thermochromic material, which consists of an electron donating compound, an electron accepting compound, and an organic medium enabling a reversible color-forming reaction between said compounds and which has a luminocity of 6 or lower in the color-developed state and a luminocity of 8 or higher in the color-extinguished state, and a film forming material.

2. A thermochromic laminate member according to claim 1, capable of reversible change between a metallic luster color and a colorless state, comprising:

A) a first layer for regulating the wavelength of reflected light, selected from a group consisting of (a) a metallic luster coated layer obtained by a coating composition composed of a metallic luster pigment, which consists of natural mica particles surfacially coated with titanium oxide and which has a particle size of 5 to 100 $\mu$m, a film forming material and a vehicle, and (b) a metallic luster sheet molded from a metallic luster pigment, which consists of natural mica particles surfacially coated with titanium oxide and which has a particle size of 5 to 100 $\mu$m, and synthetic resin; and B) a second layer selected from a group consisting of (A) a coated layer obtained from a coating composition composed of a thermochromic material, which consists of an electron donating compound, an electron accepting material and an organic medium capable of causing a reversible color-forming reaction between said compounds and which has a luminocity of 6 or lower in the color-developed state and a luminocity of 8 or higher in the color-extinguished state, a film forming material and a vehicle, and (b) a thermochromic sheet molded from a thermochromic material, which consists of an electron donating compound, an electron accepting compound and an organic medium capable of causing a reversible color-forming reaction between said compounds and which has a luminocity of 6 or lower in the color-developed state and a luminocity of 8 or higher in the color-extinguished state, and synthetic resin.

3. A thermochromic laminate member according to claim 1 or 2, capable of reversible change between a metallic luster color and the color of a dye or a pigment, wherein the second thermochromic layer contains a non-thermochromic colored dye or pigment mixed therein, and the mixture has a luminocity $V1$ of 6 or lower in the color-developed state and a colored luminocity $V2$ of 4 or higher in the color-extinguished state, said luminocities further satisfying a relation $V2 - V1 > 1$.

4. A therochromic laminate member according to claim 3, capable of reversible change between a metallic luster color and the color of a dye or a pigment, further comprising a non-thermochromic colored layer, which is positioned next to the thermochromic layer of said laminate member, is composed of a non-thermochromic colored dye or pigment and a film forming material, has a colored luminocity V3 of 4 or higher and satisfies a relation $V3-V4>1$, wherein V4 is the luminocity of the thermochromic material in the color-developed state.

5. A thermochromic laminate member according to claim 4, capable of reversible change between a metallic luster color and a colorless or pale yellow state or the color of a dye or a pigment, wherein the thermochromic material consists of microcapsules enclosing an electron donating compound, an electron accepting compound and an organic medium capable of causing a reversible color-forming reaction between said compounds.

6. A thermochromic granular material formed into powder state by cutting the thermochromic laminate member according to claim 5, capable of reversible change between a metallic luster color and a colorless state or the color of a dye or a pigment.

7. A thermochromic fiber formed by cutting the thermochromic laminate member according to claim 5, capable of reversible change between a metallic luster color and a colorless state or the color of a dye or a pigment.

8. A thermochromic laminate member according to claim 5, wherein the metallic luster pigment is selected from a group consisting of a gold luster pigment consisting of natural mica particles surfacially coated with titanium oxide of 41–44 wt. % with an optical thickness of 180–240 nm, and having a particle size of 5–60 μm, a gold luster pigment consisting of natural mica particles surfacially coated with titanium oxide of 30–48 wt. % with an optical thickness of 140–240 nm, and having a particle size of 5–60 μm, a gold luster pigment consisting of natural mica particles surfacially coated with titanium oxide of 30–48 wt. % and further with a non-thermochromic colored pigment of 0.5–10 wt. %, with a combined optical thickness of 140–240 nm, and having a particle size of 5–60 μm, a silver luster pigment consisting of natural mica particles surfacially coated with titanium oxide of 16–39 wt. % with an optical thickness of 110–170 nm, and having a particle size of 5–100 μm, and a metallic luster pigment consisting of natural mica particles surfacially coated with titanium oxide of 45–58 wt. % wiht an optical thickness of 245–415 nm, and having a particle size of 5–60 μm.

9. A thermochromic laminate member according to claim 8, wherein the metallic luster pigment is selected from a group consisting of a metallic luster pigment consisting of natural mica particles surfacially coated with titanium oxide of 45–58 wt. % and further with iron oxide of 4 –10 wt. % with a combined optical thickness of 245–415 nm, and having a particle size of 5–60 μm, a metallic luster pigment consisting of natural mica particles surfacially coated with titanium oxide of 45–58 wt. % and further with a non-thermochromic colored dye or pigment 0.5–10 wt. % with a combined optical thickness of 245–415 nm, and having a particle size of 5–60 μm, a metallic luster red pigment consisting of natural mica particles surfacially coated with titanium oxide of 45–47 wt. % with an optical thickness of 245–275 nm, a metallic luster purple pigment consisting of natural mica particles surfacially coated with titanium oxide of 48–50 wt. % with an optical thickness of 280–310 nm, a metallic luster blue pigment consisting of natural mica particles surfacially coated with titanium oxide of 51–54 wt. % with an optical thickness of 315–350 nm, and a metallic luster green pigment consisting of natural mica particles surfacially coated with titanium oxide of 55–58 wt. % with an optical thickness of 375–415 nm.

10. A thermochromic laminate member according to claim 5, which comprises a toy.

11. A thermochromic laminate member according to claim 5 which comprises a jewelry accessory.

12. A thermochromic laminate member according to claim 5, which comprises an artificial nail.

13. A sheet for forming thermochromic laminate member capable of reversible change between a metallic luster color and a colorless state, comprising a combination of:
A) a metallic luster sheet molded from a metallic luster pigment consisting of natural mica particles surfacially coated with titanium oxide and having a particle size of 5 to 100 μm, and synthetic resin; and
B) a thermochromic sheet molded from a therochromic material, which consists of an electron donating compound, an electron accepting compound, and an organic medium capable of causing a reversible color-forming reaction between said compounds and which has a luminocity of 6 or lower in the color-developed state and a luminocity of 8 or higher in the color-extinguished state, and synthetic resin.

14. A sheet according to claim 13 for forming thermochromic laminate member capable of reversible change between a metallic luster color and the color of a dye or a pigment, wherein the thermochromic sheet comprises, in addition to the thermochroic material, a non-thermochromic colored dye or pigment, and has a luminocity V1 of 6 or lower in the color-developed state and a luminocity V2 of 4 or higher in the color-extinguished state, wherein said luminocities satisfy a relation $V2-V1>1$.

15. Combined sheets according to claims 12 and 13, for forming a thermochromic laminate member capable of reversible change from a metallic luster color to a colorless or pale yellow state or the color of a dye or a pigment, wherein the thermochromic material consists of microcapsules enclosing an electron donating compound, an electron accepting compound and an organic medium capable of causing a reversible color-forming reaction between said compounds.

16. A sheet for forming the thermochromic laminate member according to claim 15, wherein the metallic luster pigment is selected from a group consisting of a gold luster pigment consisting of natural mica particles surfacially coated with titanium oxide of 41–44 wt. % with an optical thickness of 180–240 nm, and having a particle size of 5–60 μm, a gold luster pigment consisting of natural mica particles surfacially coated with titanium oxide of 30–48 wt. % with an optical thickness of 140–240 nm, and having a particle size of 5–60 μm, a gold luster pigment consisting of natural mica particles surfacially coated with titanium oxide of 30–48 wt. % and further with a non-thermochromic colored pigment of 0.5–10 wt. %, with a combined optical thickness of 140–240 nm, and having a particle size of 5–60 μm, a silver luster pigment consisting of natural mica particles surfacially coated with titanium oxide of 16–39 wt. % with an optical thickness of 110–170 nm, and having a particle size of 5–100 μm, and a metallic luster pigment consisting of natural mica particles surfacially coated with titanium oxide of 45–58 wt. % with an optical thickness of 245–415 nm, and having a particle size of 5–60 μm.

17. A sheet according to claim 16, wherein the metallic luster pigment is selected from a group consisting of a metallic luster pigment consisting of natural mica particles surfacially coated with titanium oxide of 45–58 wt. % and further with iron oxide of 4–10 wt. % with a combined optical thickness of 245–415 nm, and having a particle size of 5–60 μm, a metallic luster pigment consisting of natural mica particles surfacially coated with titanium oxide of 45–58 wt. % and further with a non-thermochromic colored dye or pigment 0.5–10 wt. % with a combined optical thickness of 245–415 nm, and having a particle size of 5–60 μm, a metallic luster red pigment consisting of natural mica particles surfacially coated with titanium oxide of 45–47 wt. % with an optical thickness of 245–275 nm, a metallic luster purple pigment consisting of natural mica particles surfacially coated with titanium oxide of 45–50 wt. % with an optical thickness of 280–310 nm, a metallic luster blue pigment consisting of natural mica particles surfacially coated with titanium oxide of 51–54 wt. % with an optical thickness of 315–350 nm, and a metallic luster green pigment consisting of natural mica particles surfacially coated with titanium oxide of 55–58 wt. % with an optical thickness of 375–415 nm.

18. Combined sheets according to claim 15 for forming a thermochromic laminate member, which comprise a toy.

19. Combined sheets according to claim 15 for forming a thermochromic laminate member, which comprise a jewelry accessory.

20. Combined sheets according to claim 15 for forming a thermochromic laminate member, which comprise an artificial nail.

* * * * *

UNITED STATES PATENT AND TRADEMARK OFFICE
CERTIFICATE OF CORRECTION

PATENT NO. : 5,352,649

DATED : October 4, 1994

INVENTOR(S) : YUTAKA SHIBAHASHI, ET AL.

It is certified that error appears in the above-identified patent and that said Letters Patent is hereby corrected as shown below:

ON TITLE PAGE

In [30] Foreign Application Priority Data, insert:
```
--Jun. 17, 1992  [JP]  Japan .......... 4-198894
  Jun. 17, 1992  [JP]  Japan .......... 4-198895
  Jun. 23, 1992  [JP]  Japan .......... 4-204192--.
```

In [57] ABSTRACT:
  Line 13, "luminocity" should read --luminosity--.
  Line 14, "luminocity" should read --luminosity--.

COLUMN 2

Line 1, "requires" should read --require--.
  Line 28, "stationary" should read --stationery--.
  Line 45, "luminocity" should read --luminosity--.
  Line 46, "luminocity" should read --luminosity--.
  Line 52, "composed" should be deleted.
  Line 53, "pound" should read --pound composed--.
  Line 68, "luminocity" should read --luminosity--.

COLUMN 3

Line 1, "luminocity" should read --luminosity--.
  Line 8, "luminocity" should read --luminosity--.
  Line 10, "luminocity" should read --luminosity--.
  Line 17, "luminocity V1" should read --luminosity V1--.
  Line 18, "luminocity V2" should read --luminosity V2--.
  Line 19, "luminocities" should read --luminosities--.
  Line 28, "luminocity V3" should read --luminosity V3--.
  Line 30, "luminocity" should read --luminosity--.

UNITED STATES PATENT AND TRADEMARK OFFICE
CERTIFICATE OF CORRECTION

PATENT NO. : 5,352,649
DATED : October 4, 1994
INVENTOR(S) : YUTAKA SHIBAHASHI, ET AL.

It is certified that error appears in the above-identified patent and that said Letters Patent is hereby corrected as shown below:

COLUMN 3

Line 58, "wiht" should read --with--.
Line 65, "luminocity" should read --luminosity--.
Line 66, "luminocity" should read --luminosity--.

COLUMN 4

Line 7, "luminocity V1" should read --luminosity V1--.
Line 8, "luminocity V2" should read --luminosity V2--.
Line 9, "luminocities" should read --luminosities--.
Line 26, "pound sand" should read --pounds and-- and "luminocity" should read --luminosity--.
Line 27, "luminocity" should read --luminosity--.
Line 34, "luminocity" should read --luminosity--.
Line 36, "luminocity" should read --luminosity--.
Line 38, "luminocity V1" should read --luminosity V1--.
Line 40, "luminocity V2" should read --luminosity V2--.
Line 41, "luminocities" should read --luminosities--.
Line 45, "luminocity V3" should read --luminosity V3--.
Line 47, "luminocity" should read --luminosity--.
Line 50, "aspect 8" should read --aspects 8--.

COLUMN 5

Line 4, "luminocity" should read --luminosity--.
Line 5, "luminocity" should read --luminosity--.
Line 7, "for according" should read --according--.
Line 13, "luminocity V1" should read --luminosity V1--.
Line 14, "luminocity V2" should read --luminosity V2--.
Line 15, "luminocities" should read --luminosities--.
Line 30, "luminocity" should read --luminosity--.

UNITED STATES PATENT AND TRADEMARK OFFICE
CERTIFICATE OF CORRECTION

PATENT NO. : 5,352,649
DATED : October 4, 1994
INVENTOR(S) : YUTAKA SHIBAHASHI, ET AL.

It is certified that error appears in the above-identified patent and that said Letters Patent is hereby corrected as shown below:

COLUMN 5

Line 31, "luminocity" should read --luminosity--.
　　Line 37, "luminocity" should read --luminosity--.
　　Line 38, "luminocity" should read --luminosity--.
　　Line 41, "luminocity V1" should read --luminosity V1--.
　　Line 42, "luminocity V2" should read --luminosity V2--.
　　Line 44, "luminocities" should read --luminosities--.
　　Line 47, "luminocity V3" should read --luminosity V3--.
　　Line 48, "luminocity" should read --luminosity--.
　　Line 52, "therochromic" should read --thermochromic--.
　　Line 56, "microcopsules" should read --microcapsules--.

COLUMN 6

Line 9, "5-100 m," should read --5-100 µm,--.
　　Line 21, "435-58 wt.%" should read --45-58 wt.%--.
　　Line 39, "be example" should read --for example--.

COLUMN 7

Line 32, "fomred" should read --formed--.

COLUMN 8

Line 42, "dye" should read --dye or--.
　　Line 67, "as" should read --a--.

COLUMN 9

Line 53, "reflected" should read --reflecting--.

UNITED STATES PATENT AND TRADEMARK OFFICE
CERTIFICATE OF CORRECTION

PATENT NO. : 5,352,649
DATED : October 4, 1994
INVENTOR(S) : YUTAKA SHIBAHASHI, ET AL.

It is certified that error appears in the above-identified patent and that said Letters Patent is hereby corrected as shown below:

COLUMN 11

Line 39, "acrylonitrile-" should be deleted.
Line 40, "butadiene-styrene copolymer" should be deleted.

COLUMN 12

Line 5, "materail" should read --material--.
Line 15, "acrylae-denatured" should read --acrylate-denatured--.
Line 42, "resin;" (second occ.) should read --resin,--.
Line 65, "ban ondular" should read --an undulating--.
Line 67, "knwon" should read --known--.

COLUMN 13

Line 28, "luminocity" should read --luminosity--.

COLUMN 14

Line 25, "along" should read --alone--.
Line 52, "luminocity" should read --luminosity--.

COLUMN 15

Line 43, "luminocity" should read --luminosity--.
Line 45, "luminocity" should read --luminosity--.
Line 50, "luminocity" should read --luminosity--.
Line 53, "abosrbed," should read --absorbed,--.
Line 55, "luminocity" should read --luminosity--.
Line 61, "luminocity" should read --luminosity--.

UNITED STATES PATENT AND TRADEMARK OFFICE
CERTIFICATE OF CORRECTION

PATENT NO. : 5,352,649
DATED : October 4, 1994
INVENTOR(S) : YUTAKA SHIBAHASHI, ET AL.

It is certified that error appears in the above-identified patent and that said Letters Patent is hereby corrected as shown below:

COLUMN 15

Line 66, "luminocity" should read --luminosity--.

COLUMN 16

Line 9, "luminocity V1" should read --luminosity V1--.
   Line 10, "luminocity V2" should read --luminosity V2--.
   Line 16, "luminocity V1" should read --luminosity V1--.
   Line 19, "luminocity V2" should read --luminosity V2--.
   Line 24, "luminocity" should read --luminosity--.
   Line 26, "luminocity" should read --luminosity--.
   Line 29, "luminocity" should read --luminosity--.
   Line 31, "luminocity" should read --luminosity--.
   Line 32, "changes" should read --change--.
   Line 34, "luminocity" should read --luminosity--.
   Line 36, "luminocity" should read --luminosity--.
   Line 41, "therochromic" should read --thermochromic--.
   Line 43, "luminocity V3" should read --luminosity V3--.
   Line 45, "luminocity" should read --luminosity--.
   Line 50, "luminocity" should read --luminosity--.
   Line 52, "luminocity" should read --luminosity--.
   Line 57, "luminocity" should read --luminosity--.
   Line 58, "luminocity" should read --luminosity--.
   Line 59, "luminocity" should read --luminosity--.
   Line 61, "a" should read --an--.
   Line 66, "luminocity" should read --luminosity--.

COLUMN 17

Line 4, "luminocity" should read --luminosity--.
   Line 9, "luminocity" should read --luminosity--.

UNITED STATES PATENT AND TRADEMARK OFFICE
CERTIFICATE OF CORRECTION

PATENT NO. : 5,352,649

DATED : October 4, 1994

INVENTOR(S) : YUTAKA SHIBAHASHI, ET AL.

It is certified that error appears in the above-identified patent and that said Letters Patent is hereby corrected as shown below:

COLUMN 17

Line 14, "luminocity" should read --luminosity--.
    Line 23, "zylene" should read --xylene--.
    Line 27, "luminocity" should read --luminosity--.
    Line 28, "luminocities" should read --luminosities--.
    Line 38, "spary" should read --spray--.
    Line 39, "luminocity" should read --luminosity-- and "thermochrmoic" should read --thermochromic--.
    Line 40, "luminocities" should read --luminosities--.
    Line 48, "methylisobutylketon" should read --methylisobutylketone--.
    Line 51, "luminocity" should read --luminosity-- and "non-thermochroic" should read --non-thermochromic--.
    Line 53, "luminocity" should read --luminosity--.
    Line 66, "example" should read --example applied--.

COLUMN 18

Line 7, "loiwng" should read --lowing-- and "part" should read --parts--.
    Line 26, "therochromic" should read --thermochromic--.
    Line 32, "luminocities" should read --luminosities--.
    Line 52, "luminocities" should read --luminosities--.
    Line 63, "luminocities" should read --luminosities--.

COLUMN 19

Line 8, "luminocities" should read --luminosities--.
    Line 29, "1" should be deleted.
    Line 31, "ion" should read --iron--.
    Line 39, "luminocities" should read --luminosities

UNITED STATES PATENT AND TRADEMARK OFFICE
CERTIFICATE OF CORRECTION

PATENT NO. : 5,352,649
DATED : October 4, 1994
INVENTOR(S) : YUTAKA SHIBAHASHI, ET AL.

It is certified that error appears in the above-identified patent and that said Letters Patent is hereby corrected as shown below:

COLUMN 19

Line 60, "luminocities" should read --luminosities--.

COLUMN 20

Line 11, "luminocities" should read --luminosities--.
Line 29, "luminocities" should read --luminosities--.
Line 48, "luminocity" should read --luminosity--.
Line 62, "luminocity" should read --luminosity--.

COLUMN 21

Line 4, "luminocities" should read --luminosities--.
Line 21 "luminocity" should read --luminosity--.
Line 25, "wavelength" should read --wavelengths--.
Line 26, "thermochroic" should read --thermochromic--.
Line 36, "luminocity" should read --luminosity-- and "theroch-" should read --thermochromic--.
Line 37, "romic" should be deleted.
Line 55, "dibutylaminofluorange," should read --dibutylaminofluorane,--.
Line 58, "luminocities" should read --luminosities--.
Line 63, "wavelengths," should read --wavelengths was absorbed,--.

COLUMN 22

Line 5, "luminocities" should read --luminosities--.
Line 11, "lwoer," should read --lower,--.
Line 25, "luminocity" should read --luminosity--.
Line 57, "regin" should read --resin--.

UNITED STATES PATENT AND TRADEMARK OFFICE
CERTIFICATE OF CORRECTION

PATENT NO. : 5,352,649
DATED : October 4, 1994
INVENTOR(S) : YUTAKA SHIBAHASHI, ET AL.

It is certified that error appears in the above-identified patent and that said Letters Patent is hereby corrected as shown below:

COLUMN 22

Line 61, "luminocities" should read --luminosities--.
Line 67, "wavelengths," should read --wavelengths was absorbed,--.

COLUMN 23

Line 7, "luminocities" should read --luminosities--.
Line 18, "luminocities" should read --luminosities--.
Line 29, "luminocities" should read --luminosities--.
Line 58, "luorescent" should read --fluorescent--.
Line 59, "luminocities" should read --luminosities--.
Line 65, "length" should read --lengths--.

COLUMN 24

Line 10, "athermally" should read --a thermally--.
Line 12, " wiht luminocities" should read --with luminosities--.
Line 14, "color-distinguished" should read --color-extinguished--.
Line 31, "luminocities" should read --luminosities--.
Line 48, "luminocities" should read --luminosities--.
Line 52, "hgiher," should read --higher,--.
Line 67, "luminocity" should read --luminosity--.

COLUMN 25

Line 13, "luminocity" should read --luminosity--.
Line 24, "luminocities" should read --luminosities--.
Line 27, "consisting" should read --constituting--.
Line 29, "wavelength" should read --wavelengths--.

UNITED STATES PATENT AND TRADEMARK OFFICE
CERTIFICATE OF CORRECTION

PATENT NO. : 5,352,649

DATED : October 4, 1994

INVENTOR(S) : YUTAKA SHIBAHASHI, ET AL.

It is certified that error appears in the above-identified patent and that said Letters Patent is hereby corrected as shown below:

COLUMN 25

Line 39, "luminocity" should read --luminosity--.
Line 55, "luminocity" should read --luminosity--.

COLUMN 26

Line 9, "luminocities" should read --luminosities--.
Line 30, "light while" should read --light was reflected while-- and "wavelength" should read --wavelengths--.
Line 41, "luminocity" should read --luminosity--.
Line 42, "developer" should read --developed--.
Line 44, "light while" should read --light was reflected while--.

COLUMN 27

Line 10, "luminocities" should read --luminosities--.
Line 16, "wavelength" should read --wavelengths--.

COLUMN 28

Line 10, "luminocities" should read --luminosities--.
Line 12, "stae." should read --state.--.
Line 17, "reproduce" should read --reproduced--.
Line 19, "2-animino-" should read --2-anilino- --.
Line 23, "luminocities" should read --luminosities--.
Line 35, "luminocities" should read --luminosities--.
Line 46, "luminocities" should read --luminosities--.
Line 61, "luminocities" should read --luminosities--.
Line 65, "light 6" should read --light 5--.

UNITED STATES PATENT AND TRADEMARK OFFICE
CERTIFICATE OF CORRECTION

PATENT NO. : 5,352,649
DATED : October 4, 1994
INVENTOR(S) : YUTAKA SHIBAHASHI, ET AL.

It is certified that error appears in the above-identified patent and that said Letters Patent is hereby corrected as shown below:

COLUMN 29

Line 16, "cities" should read --sities--.
Line 29, "ion" should read --iron--.
Line 37, "luminocities" should read --luminosities--.
Line 38, "color developed" should read --color-developed--.
Line 59, "luminocit-" should read --luminosit- --.

COLUMN 30

Line 13, "luminocities" should read --luminosities--.
Line 37, "luminocities" should read --luminosities--.
Line 61, "luminocity" should read --luminosity--.

COLUMN 31

Line 9, "materail" should read --material--.
Line 16, "luminocities" should read --luminosities--.
Line 22, "luminocity" should read --luminosity--.
Line 26, "wavelength" should read --wavelengths--.
Line 57, "luminocity" should read --luminosity--.

COLUMN 32

Line 6, "luminocity" should read --luminosity--.
Line 23, "luminocity" should read --luminosity--.
Line 39, "luminocity" should read --luminosity--.
Line 40, "lgiht 5" should read --light 5--.
Line 62, "luminocities" should read --luminosities--.
Line 68, "ling" should read --lic--.

UNITED STATES PATENT AND TRADEMARK OFFICE
CERTIFICATE OF CORRECTION

PATENT NO. : 5,352,649

DATED : October 4, 1994

INVENTOR(S) : YUTAKA SHIBAHASHI, ET AL.

It is certified that error appears in the above-identified patent and that said Letters Patent is hereby corrected as shown below:

COLUMN 33

Line 14, "luminocit-" should read --luminosit- --.
Line 23, "sufficinetly" should read --sufficiently--.
Line 34, "lumiocity" should read --luminosity--.

COLUMN 34

Line 46, "weight," should read --weight.--.
Line 47, "indicated," should read --indicated.--.
Line 55, "black fluorescent" should read --black-fluorescent--.

COLUMN 35

Line 24, "1" should be deleted.
Line 26, "7" should be deleted.
Line 28, "3" should be deleted.
Line 31, "7" should be deleted.
Line 32, "3" should be deleted.
Line 58, "sychedelic" should read --psychedelic--.

COLUMN 36

Figure 4:
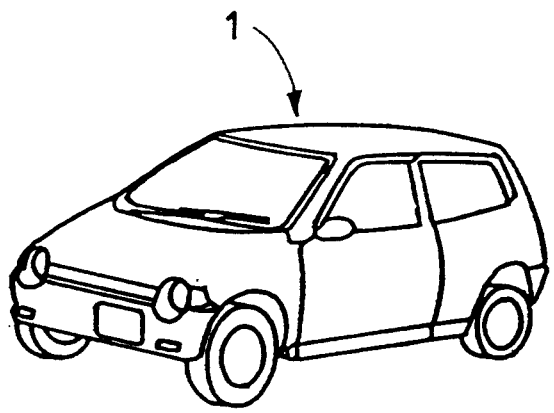
Figure 5:
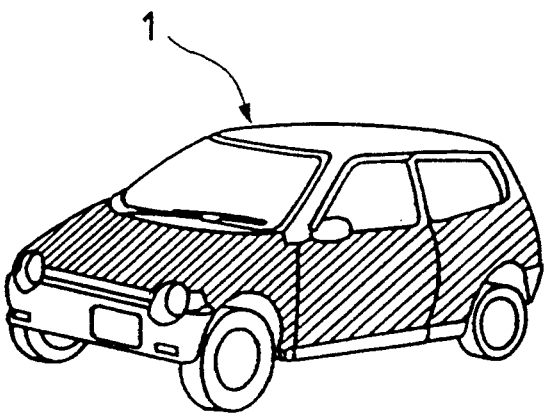

Line 17, "car" should read --car 1 (Fig. 4)--.
Line 37, "color" should read --color (Fig. 5)--.
Line 51, "acetae" should read --acetate--.

COLUMN 37

Line 1, "thermochroic" should read --thermochromic--.
Line 52, "cosisting" should read --consisting--.

UNITED STATES PATENT AND TRADEMARK OFFICE
CERTIFICATE OF CORRECTION

PATENT NO. : 5,352,649
DATED : October 4, 1994
INVENTOR(S) : YUTAKA SHIBAHASHI, ET AL.

It is certified that error appears in the above-identified patent and that said Letters Patent is hereby corrected as shown below:

COLUMN 38

Figure 6:
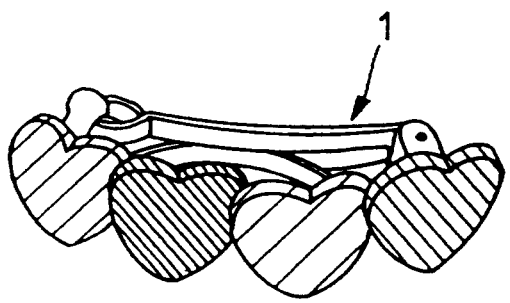

Line 15, "cooled" should read --being cooled--.
Line 23, "barrette" should read --barrette 1 (Fig. 6)--.
Line 34, "therochromic" should read --thermochromic--.

COLUMN 39

Figure 7:
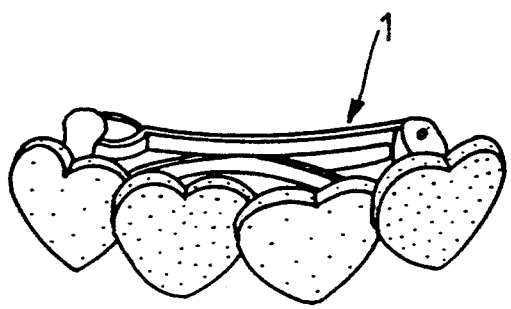

Line 25, "start" should read --star--.
Line 47, "temperature." should read --temperature (Fig. 7).--.

COLUMN 40

Line 31, "deformer" should read --defoamer--.
Line 39, "or" should read --to--.

COLUMN 41

Figure 8:
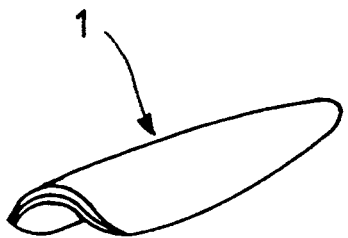
Figure 9:
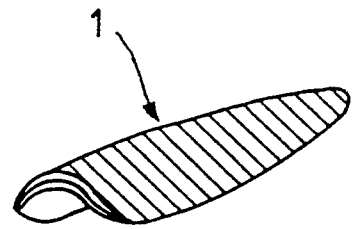

Line 27, "nail 1" should read --nail 1 (Fig. 8)--.
Line 45, "in the indoor," should read --indoors,--.
Line 49, "color" should read --color (Fig. 9)--.

COLUMN 42

Line 20, "luminocity" should read --luminosity--.
Line 21, "luminocity" should read --luminosity--.
Line 40, "(A)" should read --(a)--.
Line 47, "luminocity" should read--luminosity--.
Line 48, "luminocity" should read--luminosity--.
Line 48, "luminocity" should read --luminosity--.

UNITED STATES PATENT AND TRADEMARK OFFICE
CERTIFICATE OF CORRECTION

PATENT NO. : 5,352,649
DATED : October 4, 1994
INVENTOR(S) : YUTAKA SHIBAHASHI, ET AL.

It is certified that error appears in the above-identified patent and that said Letters Patent is hereby corrected as shown below:

COLUMN 42

Line 57, "luminocity" should read --luminosity--.
Line 62, "thermochromic" should be deleted.
Line 64, "luminocity V1" should read --luminosity V1--.
Line 66, "luminocity V2" should read --luminosity V2--.
Line 67, "luminocities" should read --luminosities--.

COLUMN 43

Line 1, "therochromic" should read --thermochromic--.
Line 8, "luminocity V3" should read --luminosity V3--.
Line 9, "luminocity" should read --luminosity--.
LIne 51, "wiht" should read --with--.
Line 63, "pigment" should read --pigment of--.

COLUMN 44

Line 13, "claim 5" should read --claim 5,--.
Line 24, "theroch-" should read --thermochromic--.
Line 25, "romic" should be deleted.
Line 29, "luminocity" should read --luminosity--.
Line 31, "luminocity" should read --luminosity--.
Line 37, "thermochroic" should read --thermochromic--.
Line 39, "luminocity V1" should read --luminosity V1--.
Line 40, "luminocity V2" should read --luminosity V2--.
Line 41, "luminocities" should read --luminosities--.

UNITED STATES PATENT AND TRADEMARK OFFICE
CERTIFICATE OF CORRECTION

PATENT NO. : 5,352,649

DATED : October 4, 1994

INVENTOR(S) : YUTAKA SHIBAHASHI, ET AL.

It is certified that error appears in the above-identified patent and that said Letters Patent is hereby corrected as shown below:

COLUMN 44

Line 43, "claims 12 and 13," should read
--claims 13 and 14,--.

Signed and Sealed this

Thirtieth Day of May, 1995

BRUCE LEHMAN

*Attest:*

*Attesting Officer*      Commissioner of Patents and Trademarks